US010959968B2

(12) United States Patent
Cardelli et al.

(10) Patent No.: US 10,959,968 B2
(45) Date of Patent: Mar. 30, 2021

(54) METHODS FOR TREATING C-MET-DEPENDENT CANCERS

(71) Applicants: Board of Supervisors of Louisiana State University and Agricultural and Mechanical College, Baton Rouge, LA (US); Board of Supervisors for the University of Louisiana System, Monroe, LA (US)

(72) Inventors: James Allen Cardelli, Shreveport, LA (US); Ana-Maria Dragoi, Shreveport, LA (US); Khalid El-Sayed, West Monroe, LA (US); Mohamed M. Mohyeldin, Alexandria (EG)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 0 days.

(21) Appl. No.: 16/070,052

(22) PCT Filed: Jan. 13, 2017

(86) PCT No.: PCT/US2017/013420
§ 371 (c)(1),
(2) Date: Jul. 13, 2018

(87) PCT Pub. No.: WO2017/123935
PCT Pub. Date: Jul. 20, 2017

(65) Prior Publication Data
US 2019/0328690 A1    Oct. 31, 2019

Related U.S. Application Data

(60) Provisional application No. 62/278,138, filed on Jan. 13, 2016.

(51) Int. Cl.
*A61K 31/192*    (2006.01)
*A61P 35/00*    (2006.01)
(Continued)

(52) U.S. Cl.
CPC ........ *A61K 31/192* (2013.01); *A61K 31/4196* (2013.01); *A61K 31/4245* (2013.01); *A61K 31/44* (2013.01); *A61P 35/00* (2018.01)

(58) Field of Classification Search
CPC .............. A61K 31/192; A61K 31/4196; A61K 31/4245; A61K 31/44; A61P 35/00
See application file for complete search history.

(56) References Cited

U.S. PATENT DOCUMENTS

2009/0163600 A1   6/2009  Maeda et al.
2013/0005771 A1   1/2013  Schwarz
(Continued)

FOREIGN PATENT DOCUMENTS

WO    2005/072723 A1    8/2005

OTHER PUBLICATIONS

Sausville & Burger. Contributions of human tumor xenograft to anticancer drug development. Cancer Research, 2006, 66: (7), Apr. 1, 2006.*

(Continued)

*Primary Examiner* — Anna Pagonakis
(74) *Attorney, Agent, or Firm* — Davis & Bujold PLLC; Charles Holoubek; Michael Bujold

(57) ABSTRACT

A method of treating cancer or a precancer condition in a mammal comprising administering a therapeutically effective amount of a homovanillyl sinapate analog or pharmacologically acceptable salt, solvate, ester, amide, clathrate, stereoisomer, enantiomer, prodrug or analog thereof, or a combination thereof.

9 Claims, 19 Drawing Sheets (-)-Oleocanthal

Homovanillyl sinapate (HVS)

(51) Int. Cl.
    *A61K 31/4196*    (2006.01)
    *A61K 31/4245*    (2006.01)
    *A61K 31/44*      (2006.01)

(56) References Cited

U.S. PATENT DOCUMENTS

2013/0272983 A1    10/2013    Okombi et al.
2013/0303611 A1    11/2013    Liu et al.
2015/0342847 A1    12/2015    Denis et al.

OTHER PUBLICATIONS

Johnson et al. Relationships between drug activity in NCI preclinical in vitro and in vivo models and early clinical trials. British Journal of Cancer, 2001, 84(10), 1424-1431.*
Dorwald F. Zaragoza. Side reviews in organic chemistry: a guide of successful synthesis design. Weinheim: WILEY-VCH, Verlag. GmbH & Co. KGaA, 2005. Preface.*
Busnena et al., "Olive secoiridoids and semisynthetic bioisostere analogues for the control of metastatic breast cancer", Bioorganic & Medicinal Chemistry, Jan. 9, 2013, vol. 21, pp. 2117-2127.
International Search Report Corresponding to PCT/US2017/013420 dated Apr. 14, 2017.
Written Opinion Corresponding to PCT/US2017/013420 dated Apr. 14, 2017.
Harris et al., Journal of Pharmaceutical Sciences, 81(1): 1-10, 1992.
American Academy of Pediatrics: Alternative Routes of Drug Administration—Advantages and Disadvantages (Subject Review), Pediatrics, 100(1): 143-152, 1997.

* cited by examiner

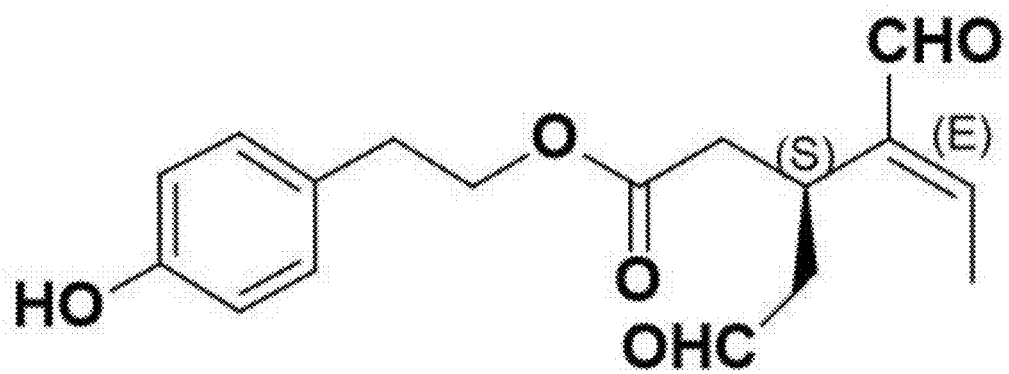
(-)-Oleocanthal
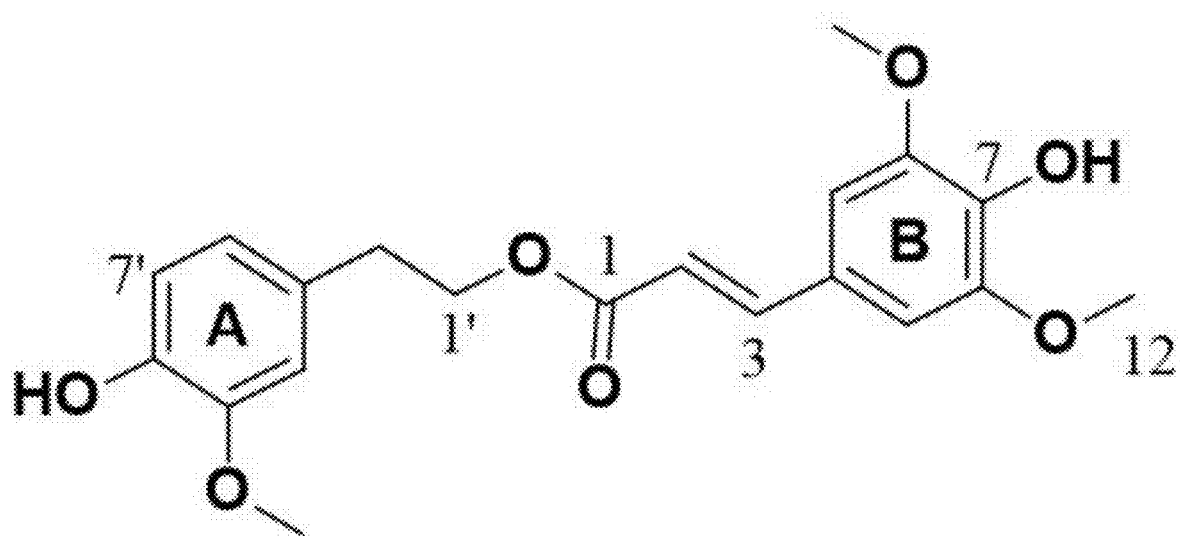
Homovanillyl sinapate (HVS)
FIG. 1B

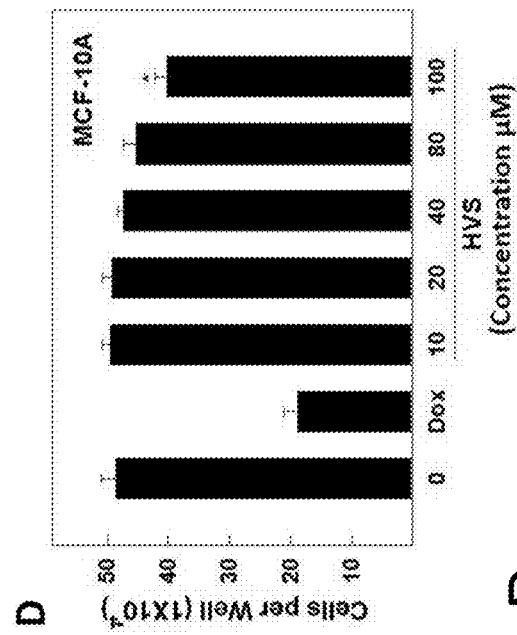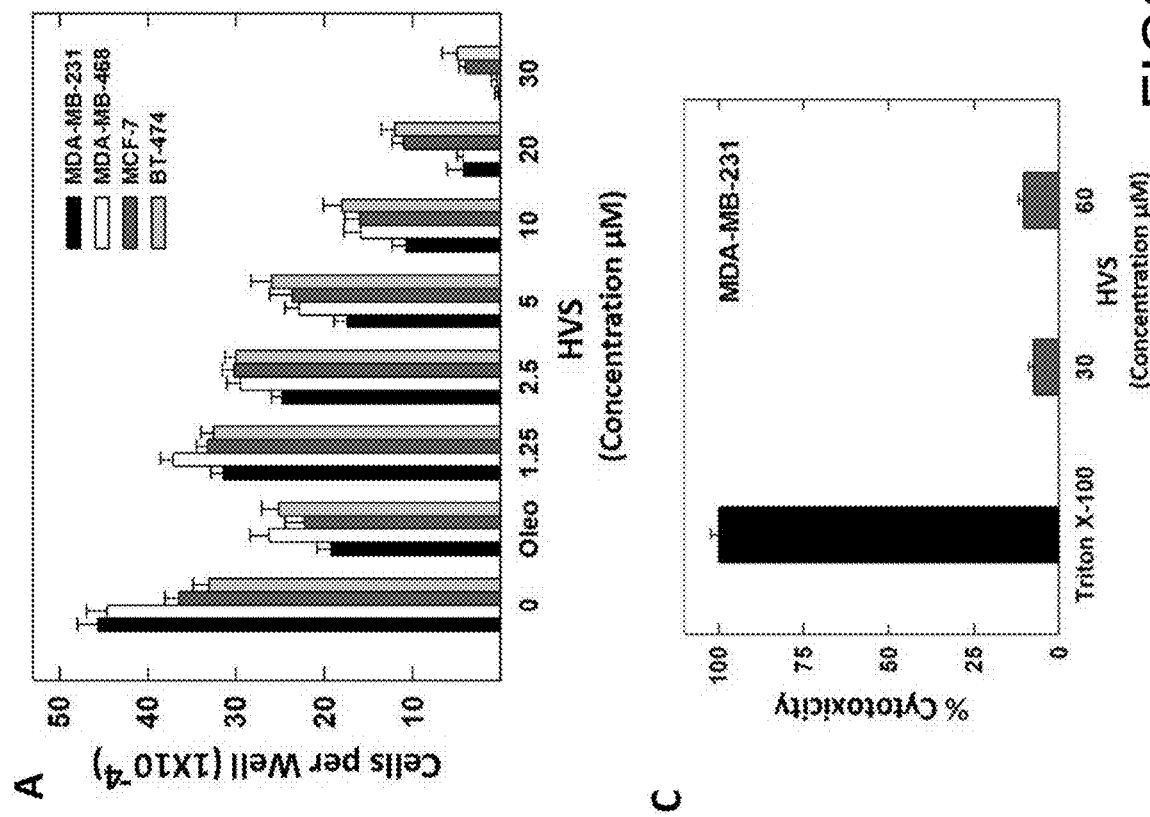
FIGS. 3A-D

FIGS. 3E-F
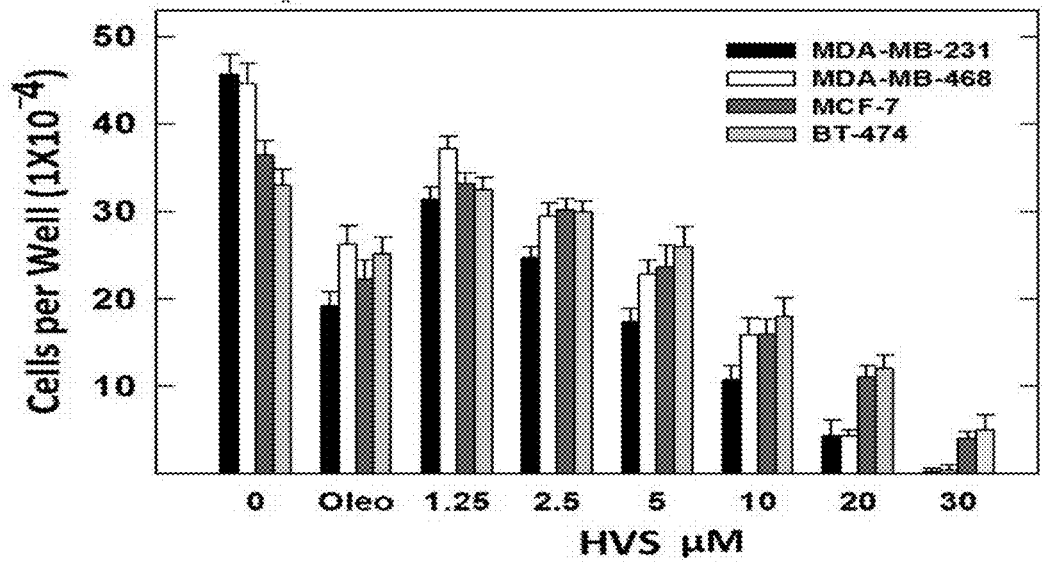
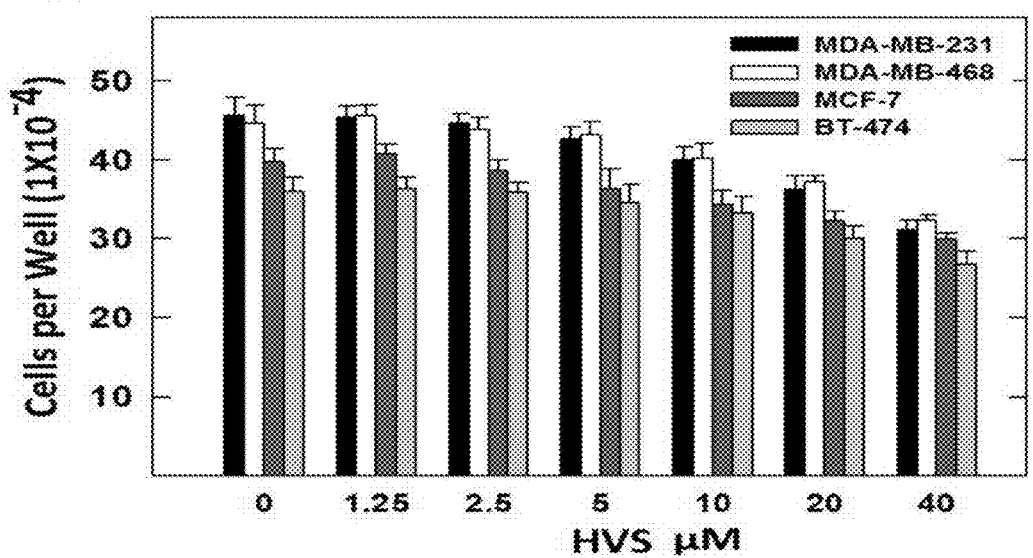
| Cell Line | HVS | Oleocanthal |
|---|---|---|
| | IC$_{50}$ (µM) | |
| MDA-MB-231 | 3.8 | 12.2 |
| MDA-MB-468 | 6 | 16.4 |
| MCF7 | 8.7 | 19.4 |
| BT-474 | 11.9 | 22.2 |

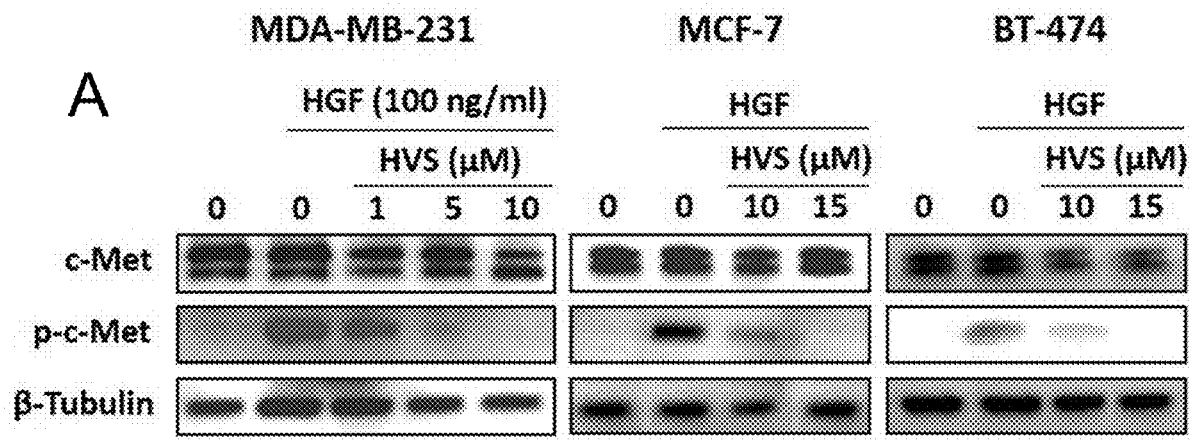
FIGS. 4A-B
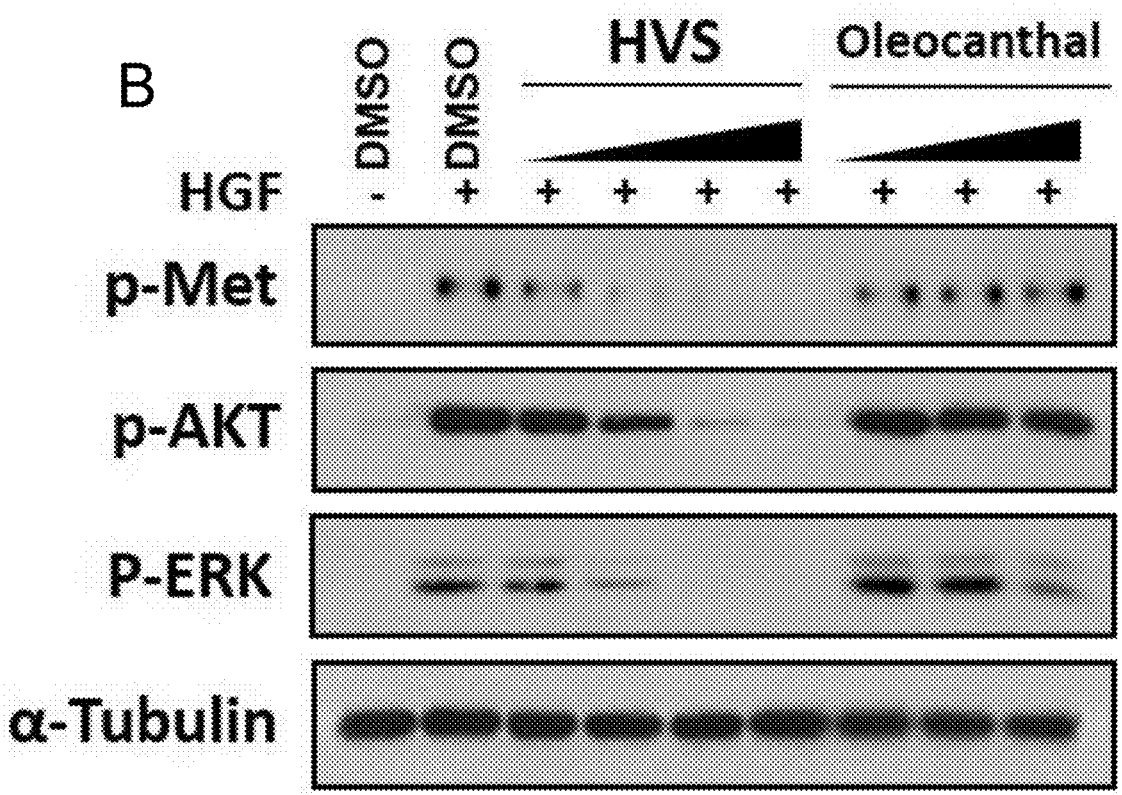

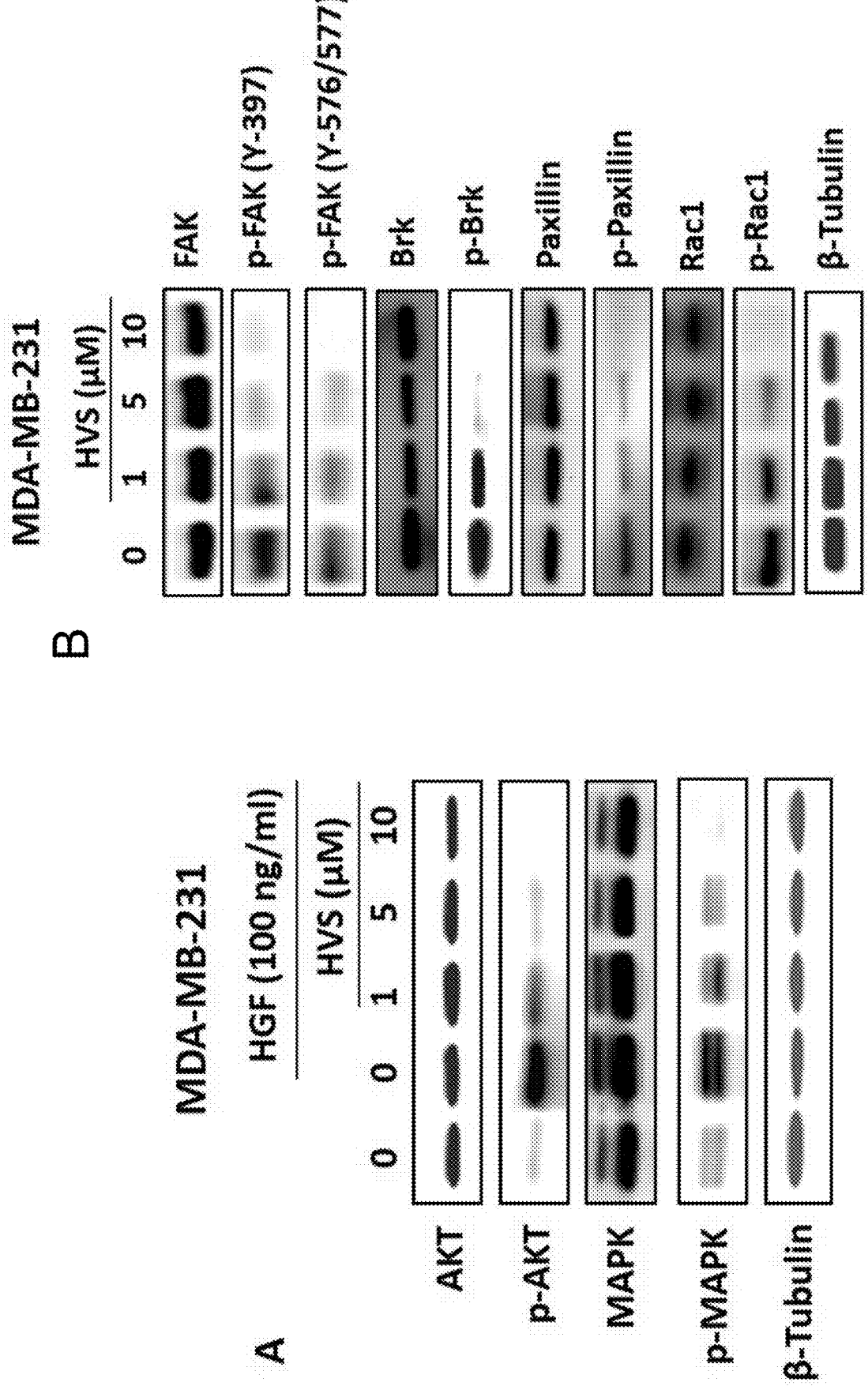
FIGS. 5A-B

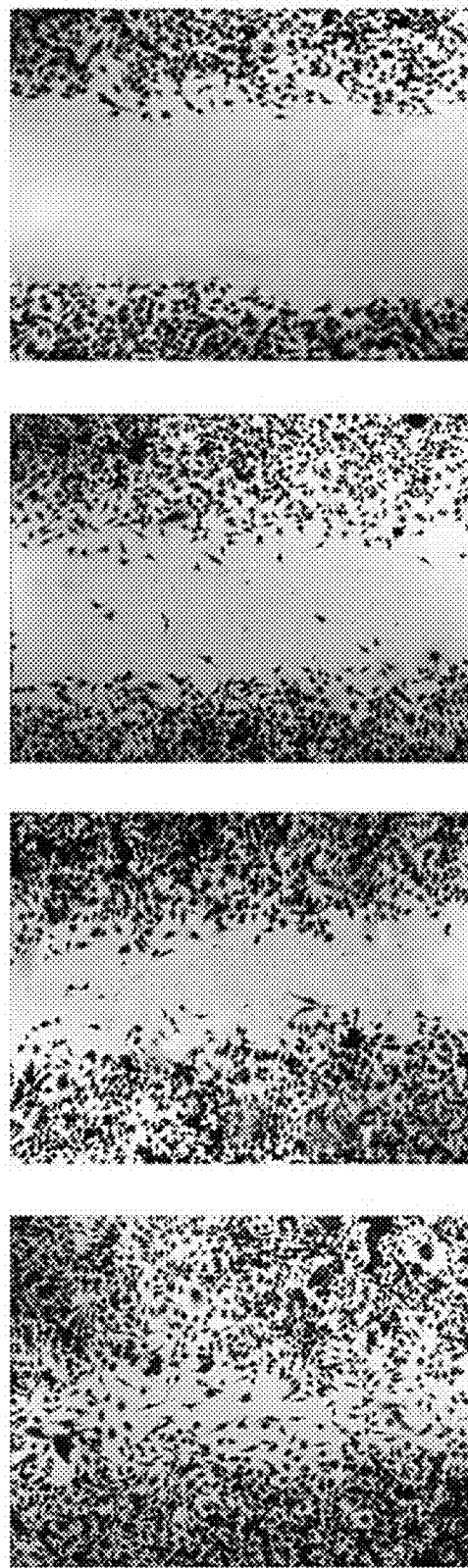
FIGS. 6A-B

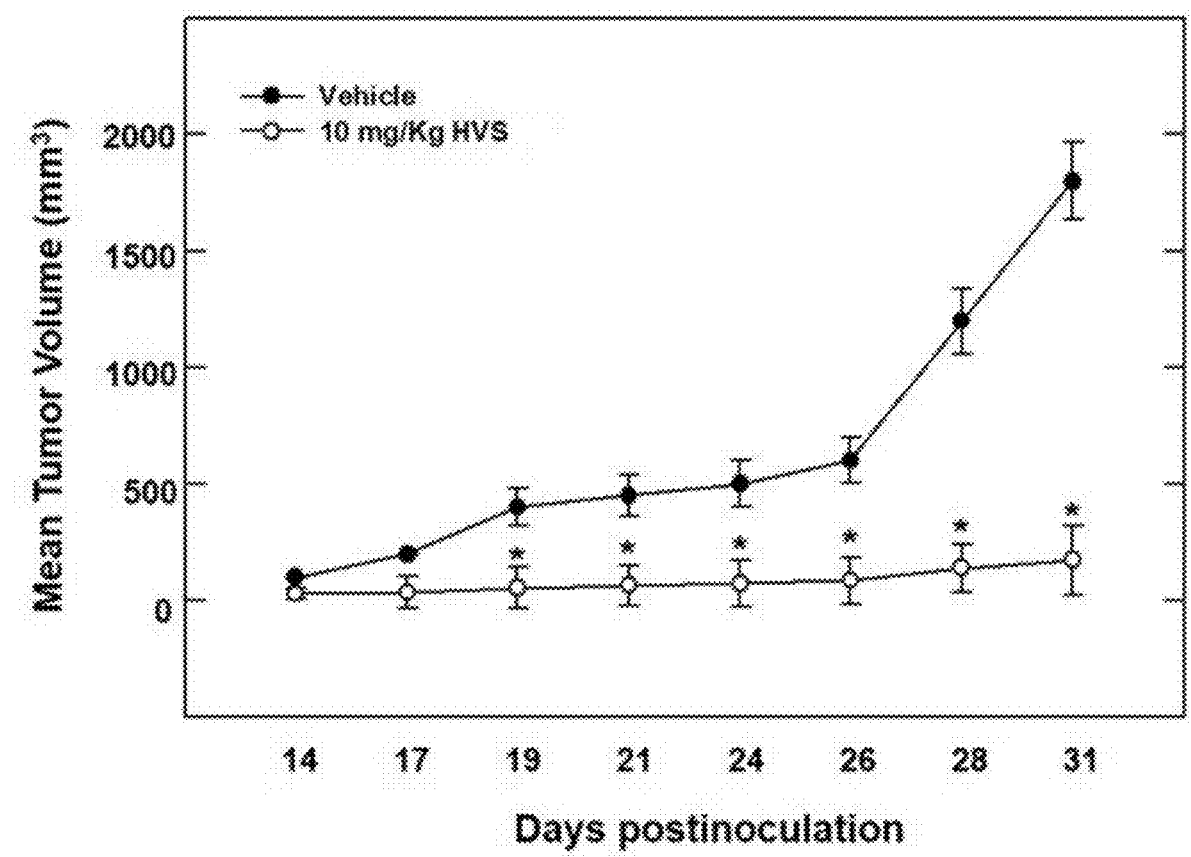
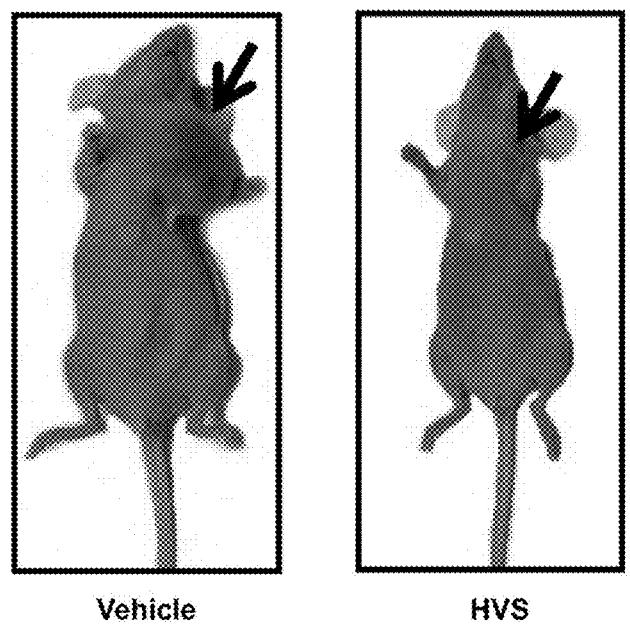
FIG. 7A

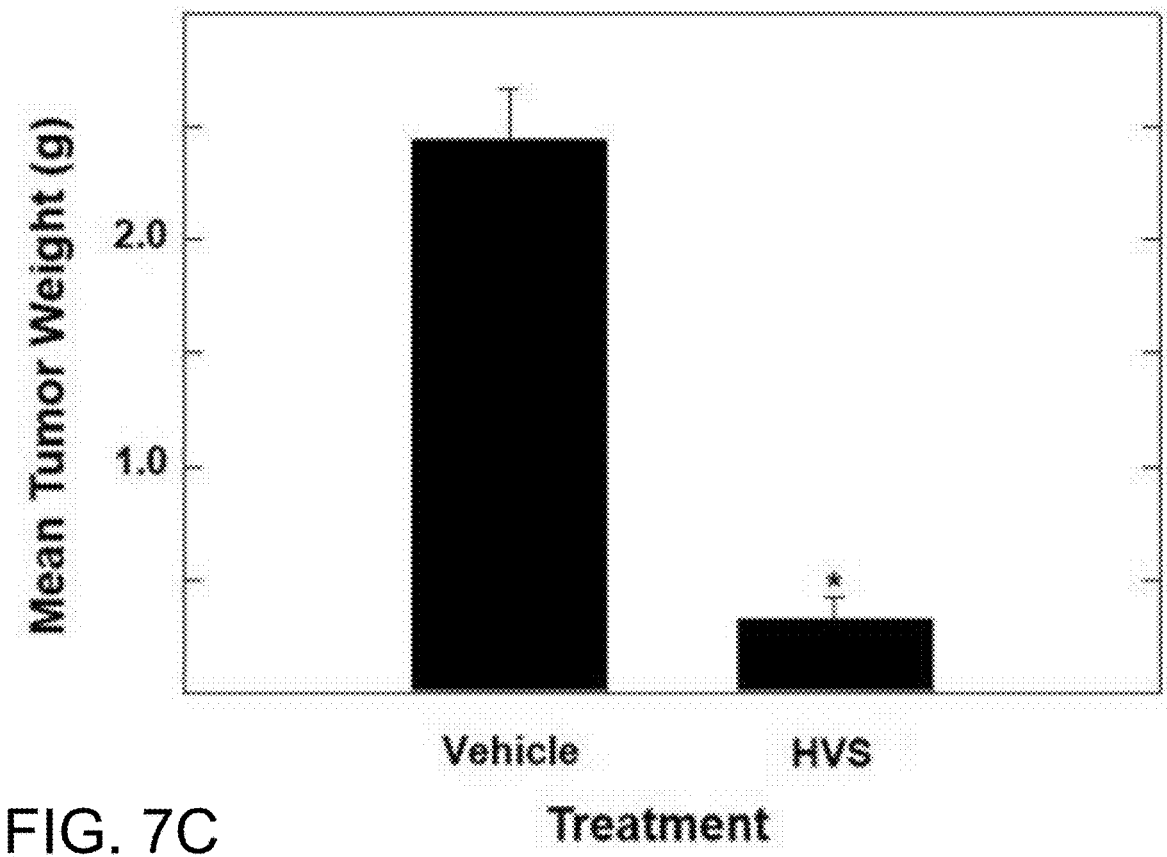
FIG. 7C
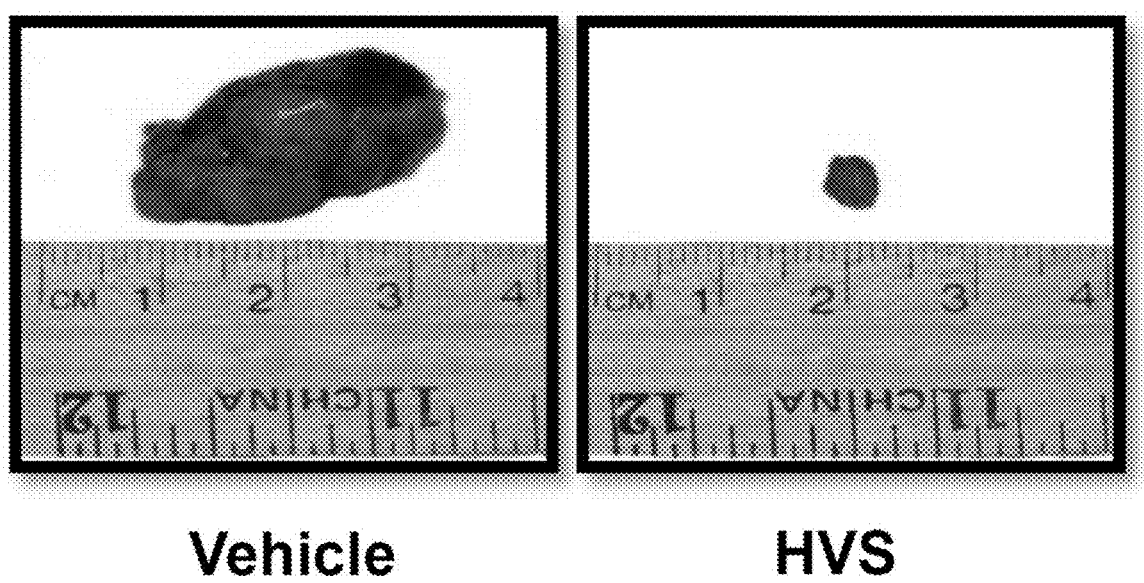

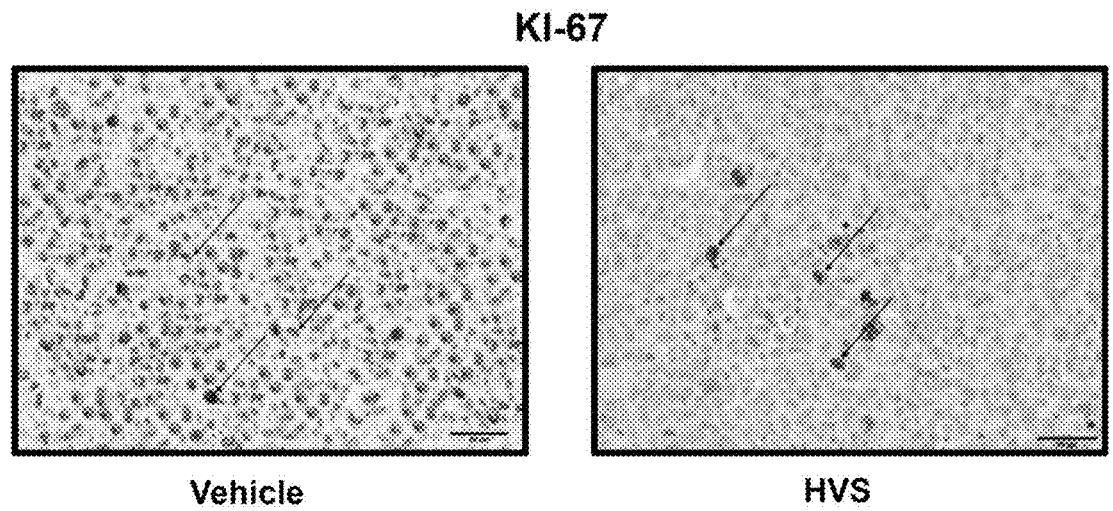
FIG. 7E-A
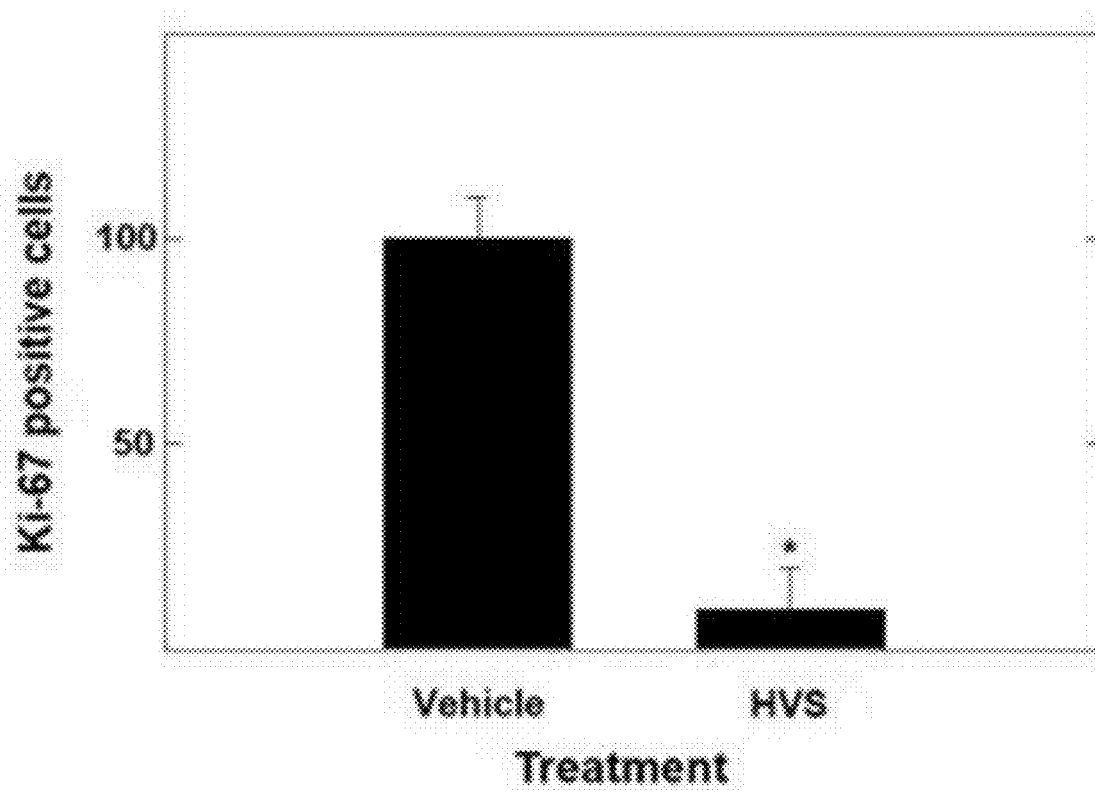

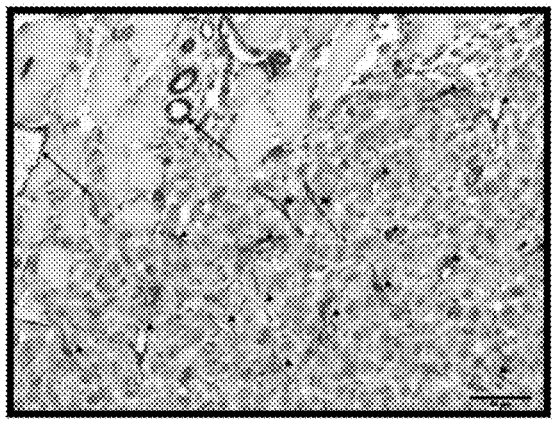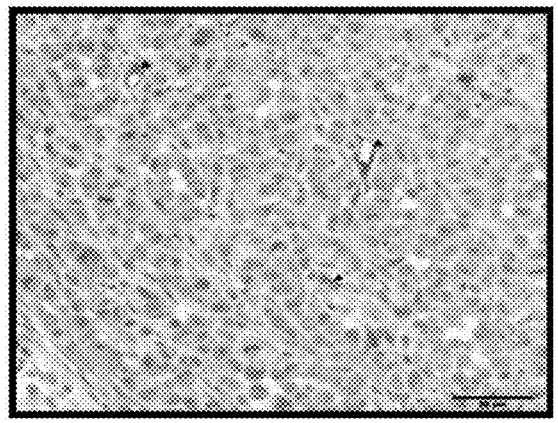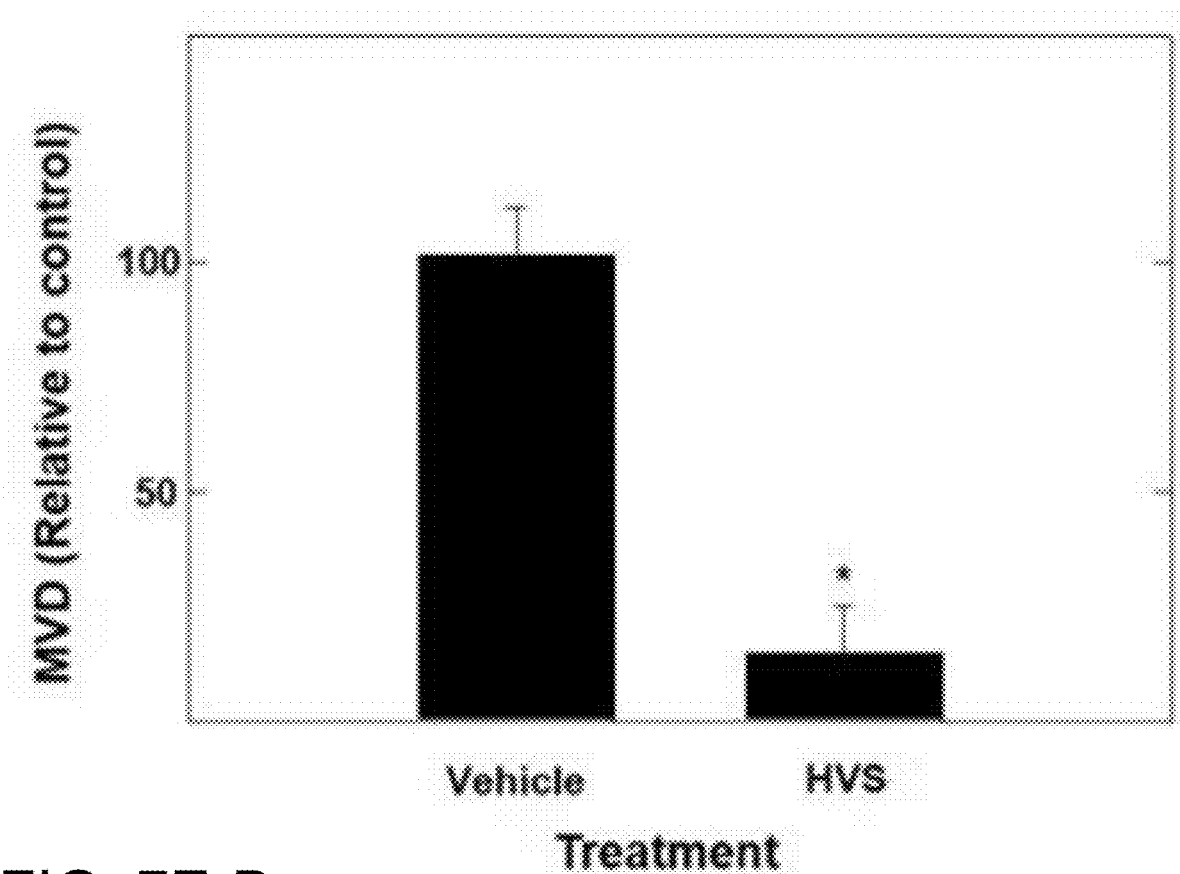
FIG. 7E-B

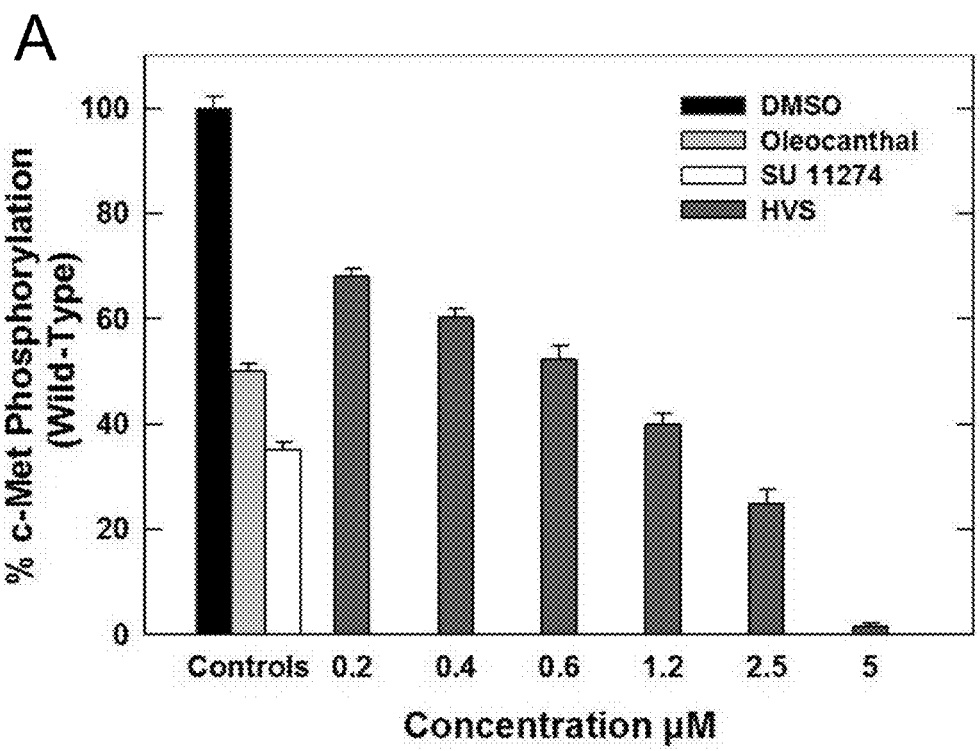
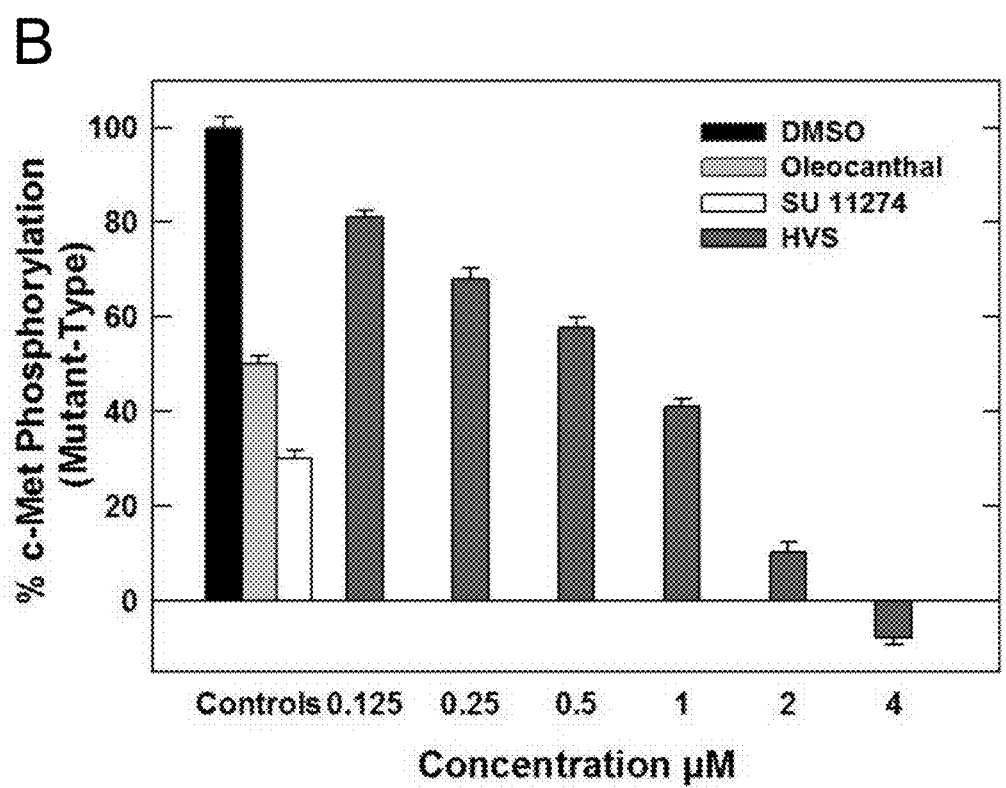
FIGS. 8A-B

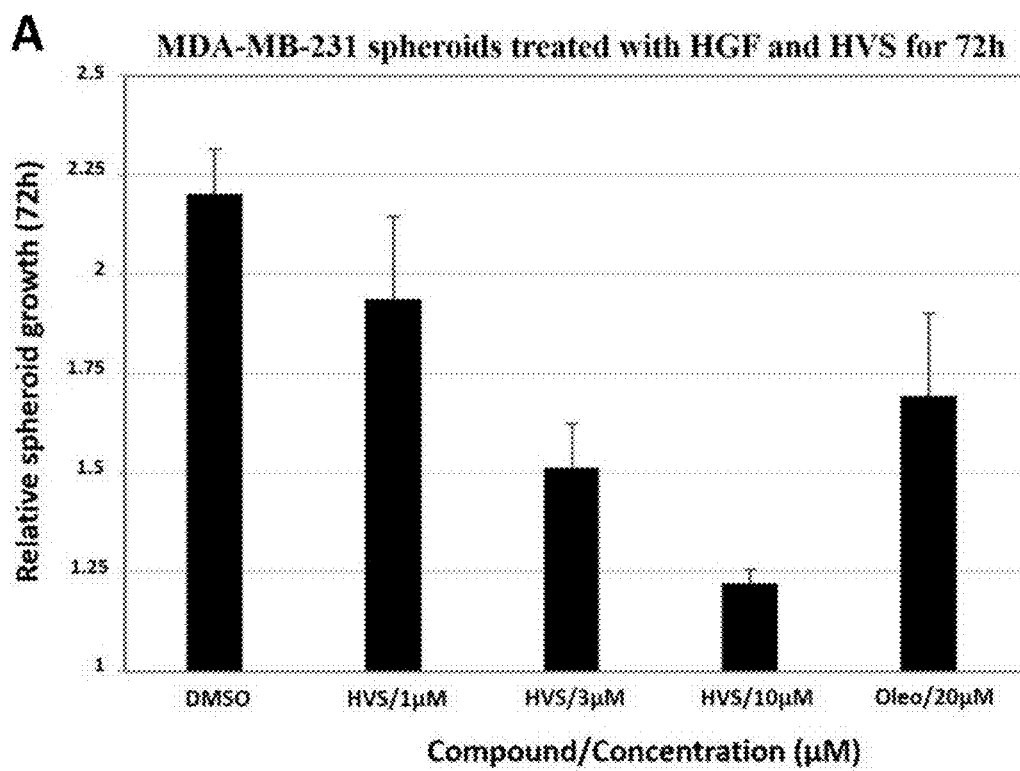
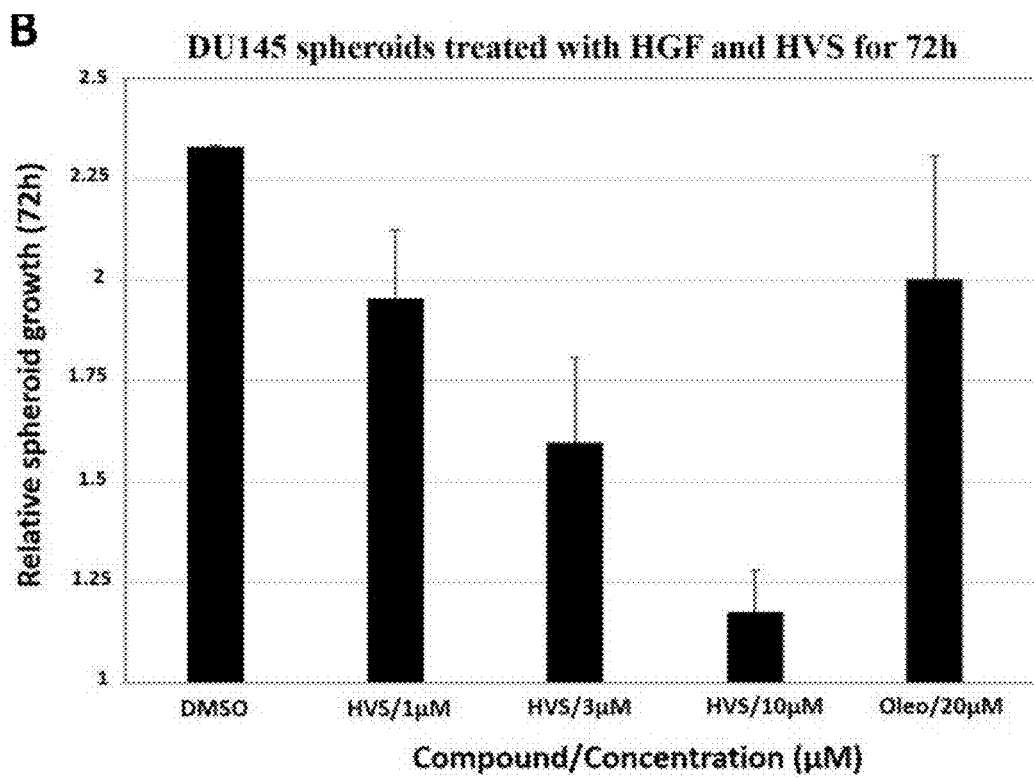
FIGS. 9A-B

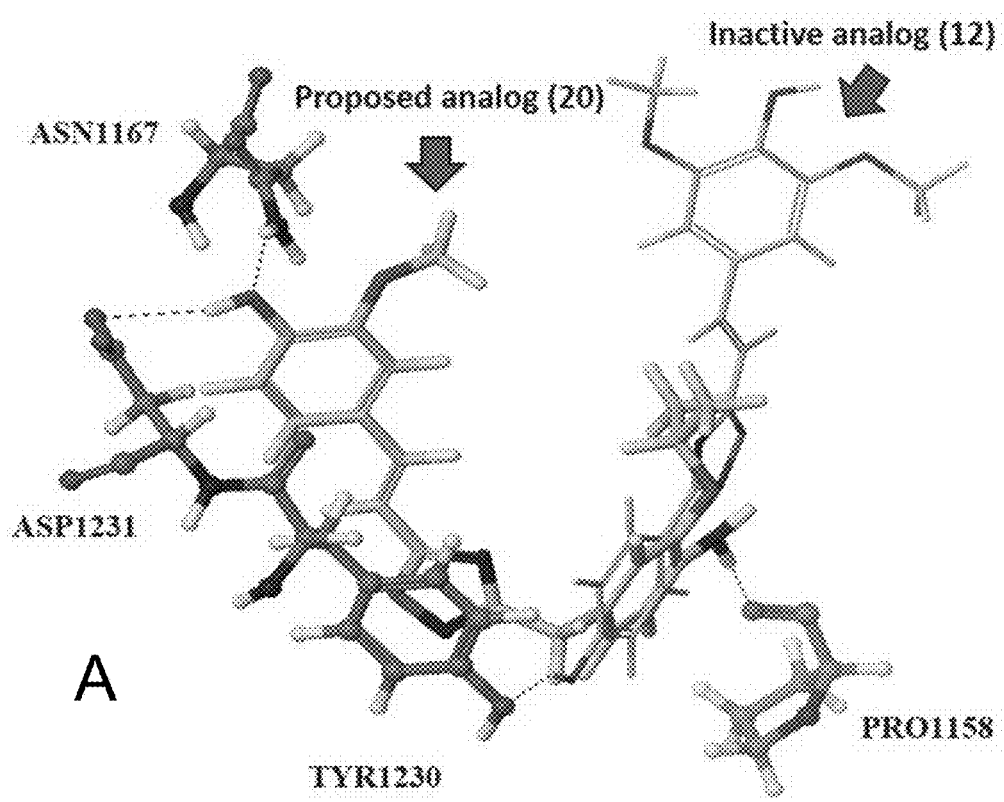
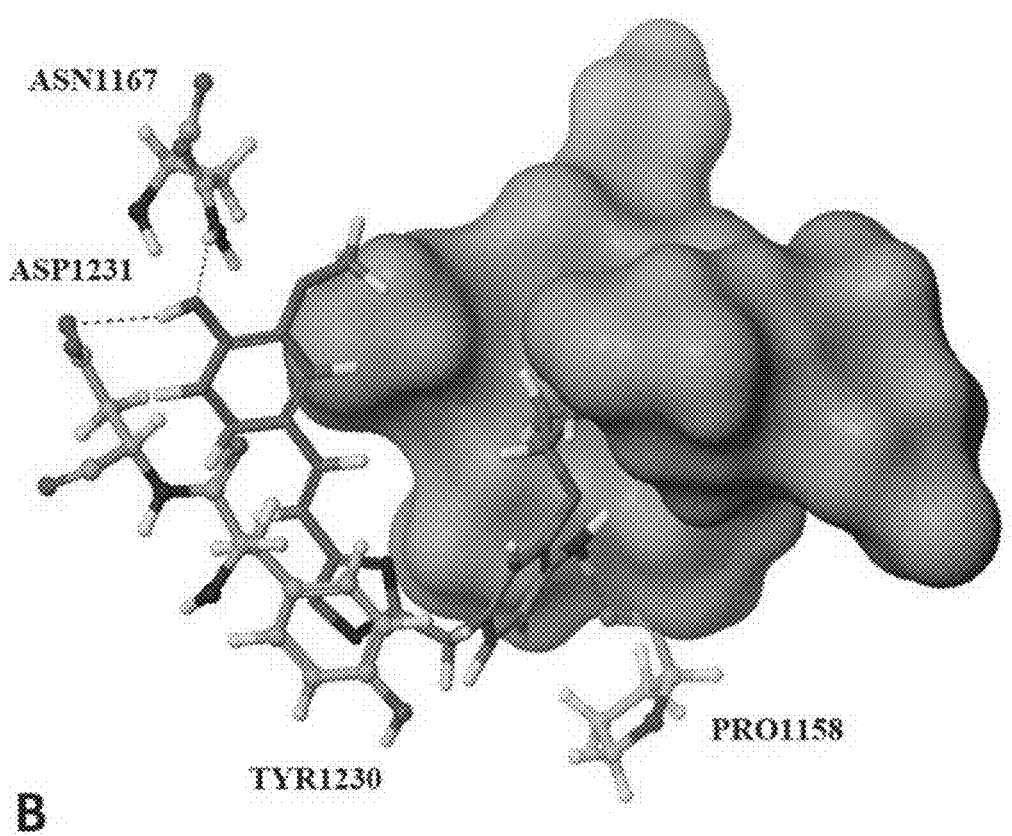
FIGS. 10A-B

METHODS FOR TREATING C-MET-DEPENDENT CANCERS

CROSS REFERENCE TO RELATED APPLICATIONS/PRIORITY

The present invention claims priority to U.S. Provisional Patent Application No. 62/278,138 filed Jan. 13, 2015, which is fully incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

FIELD

The invention generally relates to novel chemicals with anti-cancer properties and methods of treating cancer, including the pharmaceutical treatment of invasive and metastatic cancer via the dual inhibition of the oncogenic receptor, c-Met and oncogenic tyrosine kinase c-Abl.

BACKGROUND

The receptor tyrosine kinase, c-Met, has been demonstrated to play an important role in the invasion and metastasis of the vast majority of solid tumors in humans. Because of this, there has been a great deal of activity directed towards developing drugs that target the kinase activity of this receptor. Current FDA-approved c-Met inhibitors have exhibited problems with toxicity and developed resistance. There is a current, pressing need for improved c-Met inhibitor pharmaceuticals.

SUMMARY OF THE INVENTION

HGF is an important regulator of normal development and homeostasis, and dysregulated signaling through the Met receptor activates downstream pathways that contribute to cancer progression by enabling tumor cells to proliferate, survive invade and metastasize. Met is considered a top tier therapeutic target. The inventors have discovered a new class of potent c-Met inhibitors—olive phenolic synthetic derivatives (OPSDs). These include compound 8, (E)-4-hydroxy-3-methoxyph-ethyl 3-(4-hydroxy-3, 5-dimethoxyphenyl) acrylate ("homovanillyl sinapate" or "HVS"); compound 9, (E)-4-amino-3-methoxphenethyl 3-(4-hydroxyl-3, 5-dimethoxyphenyl) acrylate ("aminovanillyl sinapate" or "AVS"); and compound 10, (E)-2-(6-aminopyridin-3-yl) ethyl 3-(4-hydroxyl-3, 5-dimethoxyphenyl) acrylate ("aminopyridyl sinapate" or "APS"). Of the OPSDs, at least HVS inhibits c-Met activation as well as the oncogenic tyrosine kinase c-Abl making it a novel and potentially potent inhibitor of two oncogenes important in cancer progression.

In a preliminary assessment of the selectivity of HVS, against a panel of c-Met structurally related and oncogenically relevant tyrosine kinases, HVS has shown a significant selective inhibition of c-Met and c-Abl. Of particular note, recent studies have found that ABL kinase is activated by EGFR, IGF-1R and Src in NSCLC and breast malignancies, as a late occurring event that contributes to the aggressive growth and metastasis of these solid tumors. ABL was also proposed to interconnect oncogenic Met and p53 pathways in cancer cell. Accordingly, ABL can be considered as a point of convergence of these three pathways, and therefore, is an ideal target versus trying to target three separate pathways. Based on these data, HVS, AVS, and APS, and related homovanillyl sinapate analog ("HVSA") compounds are capable of not only targeting its primary therapeutic target, c-Met, but also of interrupting three other important pathways in solid tumor signaling, via blocking ABL1 activation, which adds a significant advantage over c-Met inhibitors currently in the clinic.

HVS, AVS, and APS and the broader HVSAs could be more efficacious in targeting c-Met driven cancers than c-Met-targeted therapies currently used in the clinic. The ability to inhibit ABL1 in addition to c-Met offers HVSAs a significant advantage over currently approved c-Met inhibitors in controlling aggressive and metastatic phenotypes of solid tumors. Additionally, is has been reported that inhibition of ABL and c-Met sensitizes solid tumor cells to conventional agents and overcomes drug resistance developed to anticancer therapies already in clinical use, including EGFR and BRAF anticancer kinase inhibitors, respectively. Therefore, a dual c-Met/ABL1 inhibitor, such as HVS and other HVSAs, not only is initially effective in slowing tumor progression, but also could prevent drug-resistant tumor growth and might be more effective if used in combination with chemotherapeutic agents, than either drug alone, for the treatment of solid tumors. Chemically, HVS is unique with its natural alcohol (homovanillyl) and natural acid (sinapic) components, which naturally occur in olive. AVS, and APS and the broader HVSAs preferably contain at least one natural acid moiety.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 3. (A) Effect of HVS treatment on HGF-stimulated growth of Met-dependent MDA-MB-231, MDA-MB-468, MCF-7. and BT-474 breast cancer cells after 72 h treatment period, compared to DMSO as vehicle control. Viable cell count was determined using MTT assay. Vertical bars indicate the mean cell count±SEM of N=3 in each treatment group; (−)-oleocanthal was used as a positive control at 20 μM. (B) Effect of HVS treatment on HGF-stimulated growth of Met-independent T-47D breast cancer cells after 72 h treatment period. Viable cell count was determined using MTT assay. Vertical bars indicate the mean cell count±SEM of N=3 in each treatment group. (C) Cytotoxic effects of HVS on the highly metastatic MDA-MB-231 breast cancer cells at two different concentrations (30 and 60 μM) using LDH cytotoxicity assay. Triton X-100 was used as a positive control to cause the breakdown of all the cells and induce the total possible LDH release. (D) Effects of HVS treatment on the viability of non-tumorigenic human MCF10A mammary epithelial cells after a 24 h treatment period, compared to DMSO as vehicle control. (E) As in panel (A) but without HGF. The table shows the IC50 for growth inhibition. Viable cell count was determined using MTT assay. Vertical bars indicate the mean cell count±SEM of N=3 in each treatment group; doxorubicin was used as a positive control at 10 μM dose. *P<0.05 as compared with vehicle treated control.

FIG. 4. A) Effect of HVS treatment on HGF-induced c-Met activation in human breast cancer cells using Western Blot analysis. Treatment with HVS caused a significant, dose-responsive inhibition of HGF-induced c-Met phosphorylation in MDA-MB-231, MCF-7, and BT-474 mammary tumor cells with no effect on total c-Met levels after treatment for 72 h, as compared to their respective vehicle-treated control groups. The visualization of β-tubulin was used as a loading control. (B) Effect of HVS on HGF-induced c-Met activation and its downstream mitogenic signaling in DU145 human prostate cancer cells, as compared to vehicle-treated control group, using Western Blot analysis. Cells were pre-treated for 30 minutes with either HVS at 0.1, 0.3, 1, and 5 μM or (−)-oleocanthal at 5, 10, and 20 μM doses in serum-free 0.4-media. 33 ng/mL HGF was then added for 30 minutes. Whole cell lysates were collected and assayed by Western Blot. The visualization of α-tubulin was used as a loading control. Representative Western Blots from each experiment are shown, N=3.

FIG. 5. Effects of HVS treatment on c-Met downstream mitogenic and FAK/Brk/paxillin/Rac1 signaling pathways in human MDA-MB-231 breast cancer cells after a treatment period of 72 h. (A) Western Blot analysis showing HVS treatment effects on c-Met downstream mitogenic signaling molecules, Akt and MAPK, using different treatment doses, compared to the vehicle-treated control group. (B) Western Blot analysis showing HVS treatment effects on FAK/Brk/Paxillin/Rac1 signaling pathway using different treatment doses, compared to the vehicle-treated control group. The visualization of β-tubulin was used as a loading control. Representative Western Blots from each experiment are shown, N=3.

FIG. 8. Mutant c-Met phosphorylation inhibition by various doses of HVS using a Z'-LYTE assay kit. Error bars indicate the SEM of n=3l dose. SU11274 was used as a positive control.

FIG. 9. (A). MDA-MB231 cells were grown in 10% FBS DMEM. Cells were collected after trypsinization and resuspended in phenol-red free DMEM with 10% FBS. Cells were labeled with CellTracker Red (Life Technologies) for 5 minutes. After labeling cells were washed with PBS and transfer into 96-well Corning 7007 ULA round bottom plates at 1,000 cells/well in 100 μl phenol-red free media with 10% FBS and 5% Matrigel. After the spheroids were established (24 h later) the following treatments were applied (8 spheroids per group): (1) DMSO control; (2) compound 8 (1 μM); (3) compound 8 (3 μM); (4) compound 8 (10 μM); (5) compound 9 (10 μM); (6) compound 10 (10 μM); (7) oleocanthal (20 μM). Spheroids were grown at 37° C. and 5% CO2 in IncuCyte ZOOM (Essen Bioscience). Images were acquired every 4 h for a period of 72 h post-treatment. The data were expressed as fold increase in spheroids size at the end of the treatment using the "average red object area in the well" as determined by the IncuCyte software analysis.

FIG. 9B: DU145 cells were grown in 10% FBS DMEM. Cells were collected after trypsinization and resuspended in phenol-red free DMEM with 10% FBS. Cells were labeled with Cell-Tracker Red (Life Technologies) for 5 minutes. After labeling cells were washed with PBS and transfer into 96-well Corning 7007 ULA round bottom plates at 1,000 cells/well in 100 μl phenol-red free media with 10% FBS and 5% Matrigel. After the spheroids were established (24 h later) the following treatments were applied (8 spheroids per group): (1) DMSO control; (2) compound 8 (1 μM); (3) compound 8 (3 μM); (4) compound 8 (10 μM); (5) compound 9 (10 μM); (6) compound 10 (10 μM); (7) oleocanthal (20 μM). Spheroids were grown at 37° C. and 5% CO2 in IncuCyte ZOOM (Essen Bioscience). Images were acquired every 4 h for a period of 72 h post-treatment and software analysis was design to identify the red object in the well. The data were expressed as fold increase in spheroids size at the end of the treatment using the "average red object area in the well" as determined by the IncuCyte software analysis.

FIG. 10: (A) Structure overlay of the inactive oxadiazole analog compound 12 with the proposed active compound 20 within the c-Met kinase ATP-binding pocket, as predicted by docking simulations. (B) In silico binding pose of compound 20 within the c-Met kinase ATP-binding site. Important hydrogen bonding interactions exerted by compound 20 are shown in blue dotted lines. The hydrophobic subpocket where the compound 20's R1 group fits is shown in solid aquamarine surface.

DETAILED DESCRIPTION OF THE INVENTION

Figure 1A:
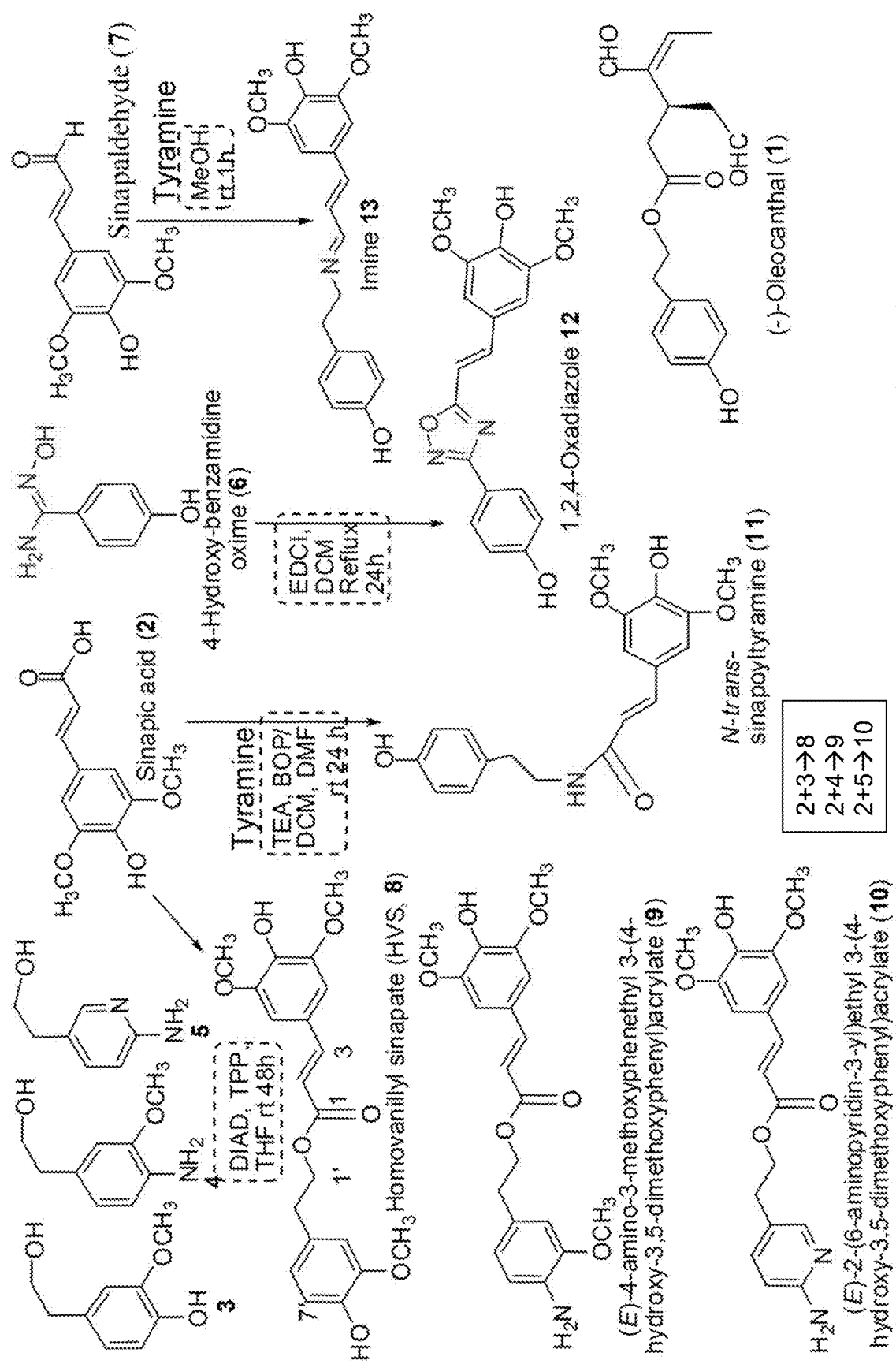
FIG. 1: Representative synthesized oleocanthal bioisostere analogs Chemical structures of (−)-oleocanthal and homovanillyl sinapate (HVS). A). The series of molecules and intermediates synthesized. B). Chemical structures for oleocanthal versus HVS.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIG. 1, a brief description concerning the various components of the present invention will now be briefly discussed. c-Met is exceptionally promising therapeutic target in anticancer drug discovery based on the mounting evidence for the involvement of c-Met overexpression and/or dysregulated activation of its signaling pathway in the development and progression of multiple types of tumors, including pancreatic, thyroid, brain, lung, breast and prostate cancers to name a few. Studies have shown that targeting c-Met signaling can prevent tumor progression and, in some cases, even reverse advanced stages of tumor progression as evidenced by a reduction in the number and size of metastatic lesions. While several c-Met inhibitors have been approved for treatment of some types of cancers, these compounds are not effective for all types of cancers. Further, it is common for some patients to become resistant to these c-Met inhibitors, so there is a need for finding more effective inhibitors of the c-Met pathway.

The inventors have discovered, through a series of semi-synthetic optimization approaches, novel bioisostere analogues hereinafter termed homovanillyl sinapate analogs (HVSA). The generic chemical structure of the HVSA is below:

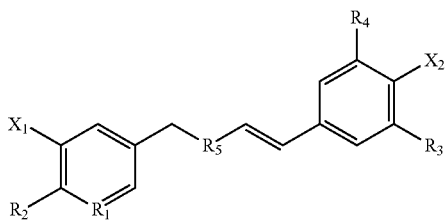

Some potential forms of the HVSAs include where $R_5$ is one of an ester, an oxadiazole and a triazole, and/or $R_1$ is one of C—H, C—OCH$_3$, N, C—OCH$_2$CH$_3$, C—OCH(CH$_3$)$_2$, and C—OC(CH$_3$)$_3$, and/or $R_2$ is one of OH, NH$_2$, CH$_2$NH$_2$, and CH$_2$OH, and/or X1 is one of H, OCH$_3$, OCH$_2$CH$_3$, OCH(CH$_3$)$_2$, and OC(CH$_3$)$_3$, and/or $R_3$ is one of H, OCH$_3$, and Br, and/or $R_4$ is one of H, and OCH$_3$, and/or $X_2$ is one of OH and NH$_2$, and/or $R_5$ is one of CH$_2$OCO, C$_2$H$_2$N$_2$O, and C$_2$H$_3$N$_3$.

The HVSAs include homovanillyl sinapate ("HVS," "compound 8"), (E)-4-amino-3-methoxyphenethyl 3-(4-hydroxy-3, 5-dimethoxyphenyl)-acrylate ("compound 9"), (E)-2-(6-aminopyridin-3-yl)ethyl 3-(4-hydroxy-3,5-dimethoxyphenyl)acrylate ("compound 10"). Other similar non-functional compounds were created also, represented by 11-13 (FIG. 1).

The chemical structure for additional ester HVSAs, labeled Chem./compound 14-19 follow.

Chem. 14

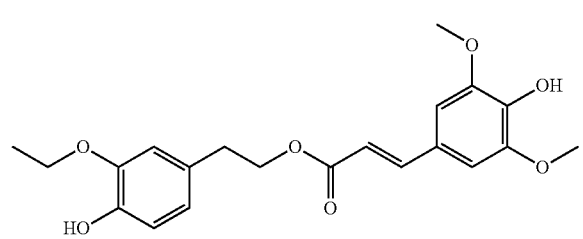

Chem. 15

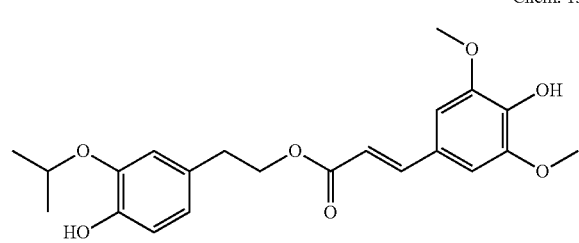

Chem. 16

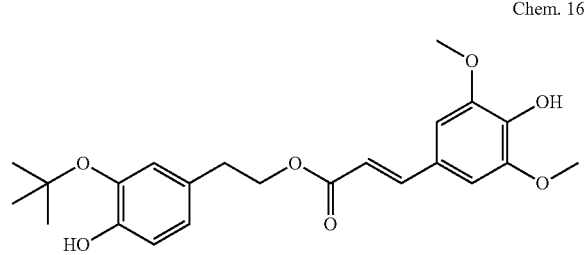

Chem. 17

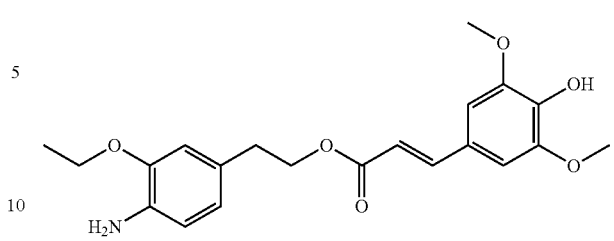

Chem. 18

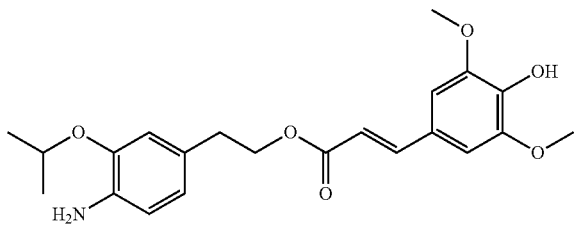

Chem. 19

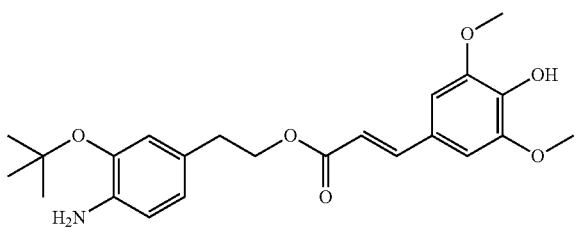

Some of the compounds shown in FIG. 1A, compounds 8-10, showed remarkable potency against wild-type recombinant human c-Met kinase and its oncogenic variant, as detailed below. The compounds are effective at preventing c-Met activation at the hundred nanomolar to low micromolar concentrations, identifying phenolic esters as a novel c-Met inhibitory entity and allowing for positioning to develop optimized lead compounds for use in the clinic for the use to control c-Met-dependent malignancies.

Figure 2:
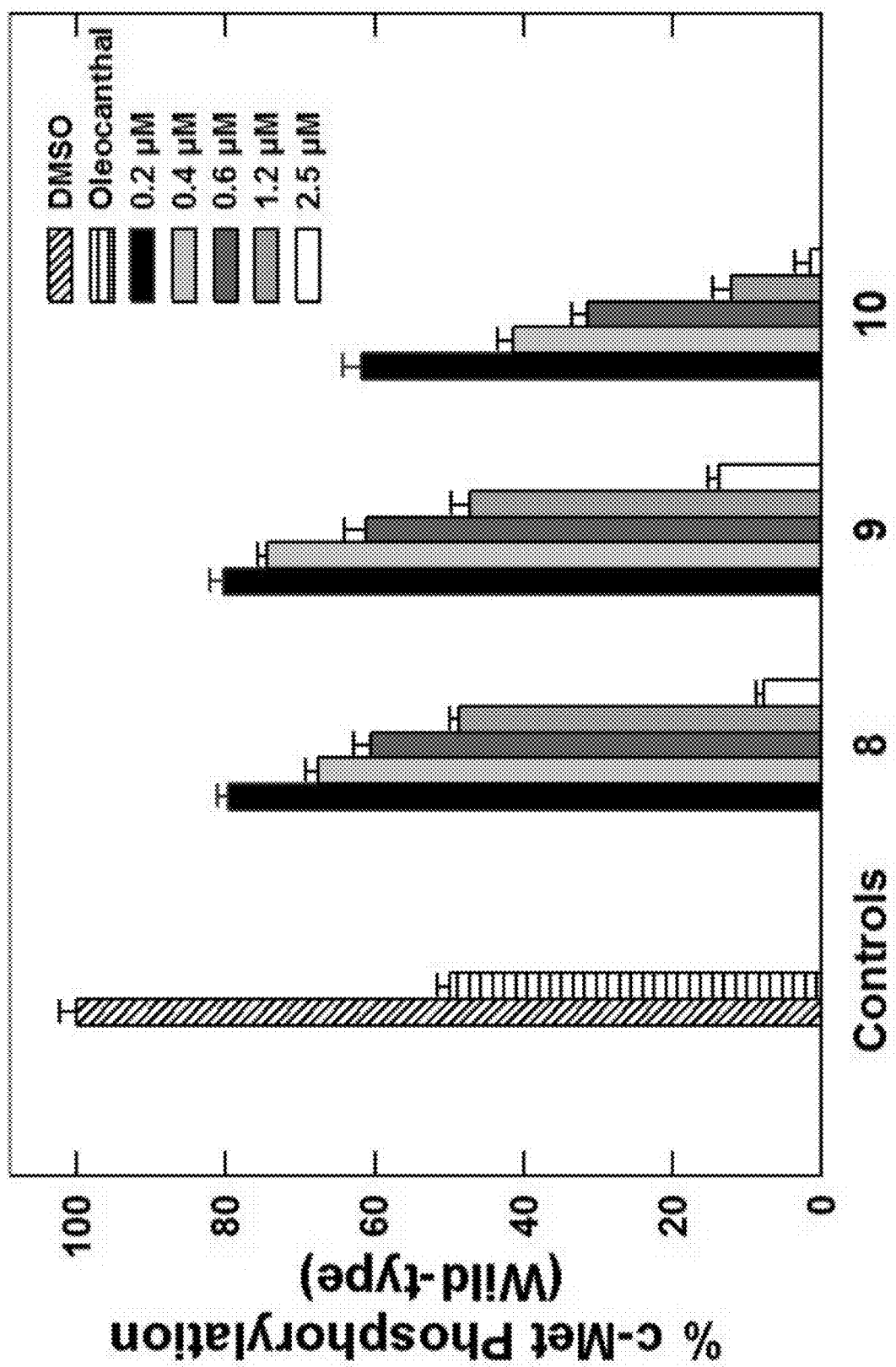
FIG. 2 A) Effect of compounds 8-10 on the phosphorylation (activation) of wild-type recombinant human c-Met kinase at different concentrations, using Z'-LYTE assay kit.

Additionally, docking and kinetic studies suggest that compounds 8-10 may work as a class I c-Met inhibitor like SU11274 by competing for the ATP-binding site of c-Met. This was further confirmed in Z-LYTE cell free assay for compounds 8-10 (FIG. 2).

In vitro assays demonstrate the ability of compounds 8-10 to significantly inhibit HGF-induced proliferation across a broad spectrum of human cancer cell lines in a dose-responsive manner (FIGS. 3E and 3F). Selection of the aforementioned breast cancer cells was based on their phenotypes. ERα is expressed in MCF-7, BT-474 and T-47D cells, whereas MDA-MB-231 and MDA-MB-468 cells lack the expression of ERα. c Met is expressed in MDA-MB-231, MDA-MB-468, MCF-7 and BT-474, while it is absent in T-47D cells. The results reveal that human cancer cells, with higher levels of c-Met expression, are the most sensitive to the antiproliferative effects of compounds 8-10 compared to those with lower c-Met levels. Compound 8 significantly inhibited HGF-induced proliferation of human breast cancer cells from lines MDA-MB-231, MDA-MB-468, MCF-7 and BT-474, with IC50 values of 3.8, 6.0, 12.2 and 15.4 µM, respectively (FIG. 3A). Similar treatment doses had no discernable effects on these cells in the absence of HGF, and no discernable effects on non-tumorigenic human MCF10A cells or T47-D cells which lack c-Met (FIGS. 3D and 3B, respectively). HVS induced minimal LDH release at 50 μM and 100 μM concentrations, respectively, in MDA-MB-231 cells (FIG. 3C). These concentrations represent several-fold HVS's antiproliferative IC50 value, suggesting lack of mitochondrial mechanism of cytotoxicity and confirming a good in vitro safety profile on non-tumorigenic cells.

The inhibition of cancer cell growth is associated with the ability of compounds 8-10 treatment to disrupt c-Met receptor phosphorylation in response to its natural ligand HGF in all investigated cancer cell lines and thus, inhibiting the downstream c-Met effectors in culture. Interestingly, the concentrations of compounds 8-10 required to induce 50% inhibition of cancer cell growth are significantly greater for cancer cells maintained in HGF-free media as compared to those maintained in media supplied with HGF. This finding indicates that compounds 8-10 treatment is dependent on the presence of HGF, confirming the compounds proposed molecular mechanism as direct inhibition of the HGF/c-Met signaling pathway.

The four human breast cancer cell lines expressing c-Met, namely MBA-MD-231, MCF-7 and BT-474, and the prostate cancer cell-line Du-145 were chosen to characterize the pharmacological effects of HVS, which were found to be mediated via inhibition of HGF-induced c-Met activation and its downstream mitogenic signaling pathways. Western blot analysis proved significant inhibition of HGF-induced c-Met phosphorylation after treatment with HVS for 72 h, compared to vehicle-treated control groups (FIG. 4A). Meanwhile, treatment with HVS did not affect total c-Met levels at the tested concentrations. HVS dose-dependently suppressed FAK, Brk, paxillin and Rac1 phosphorylation (activation) after 72-h treatment in MDA-MB-231 cancer cells (FIG. 5). On the other hand, HVS had little or no effects on the total levels of FAK, Brk, paxillin, and Rac1 in treated cells. Exposure to antiproliferative concentrations of 8 blocked HGF-induced phosphorylation and activation of Akt and MAPK in MDA-MB-231 mammary cancer cells (FIG. 5). Activation of c-Met prevents apoptosis and maintains cancer cell survival through activation of PI3K and subsequent Akt-NFκB activation. Accordingly, HVS effectively blocked mitogenesis and proliferation through suppression of HGF-induced c-Met activation and subsequent activation of downstream effectors (FIG. 5).

Figure 6C:
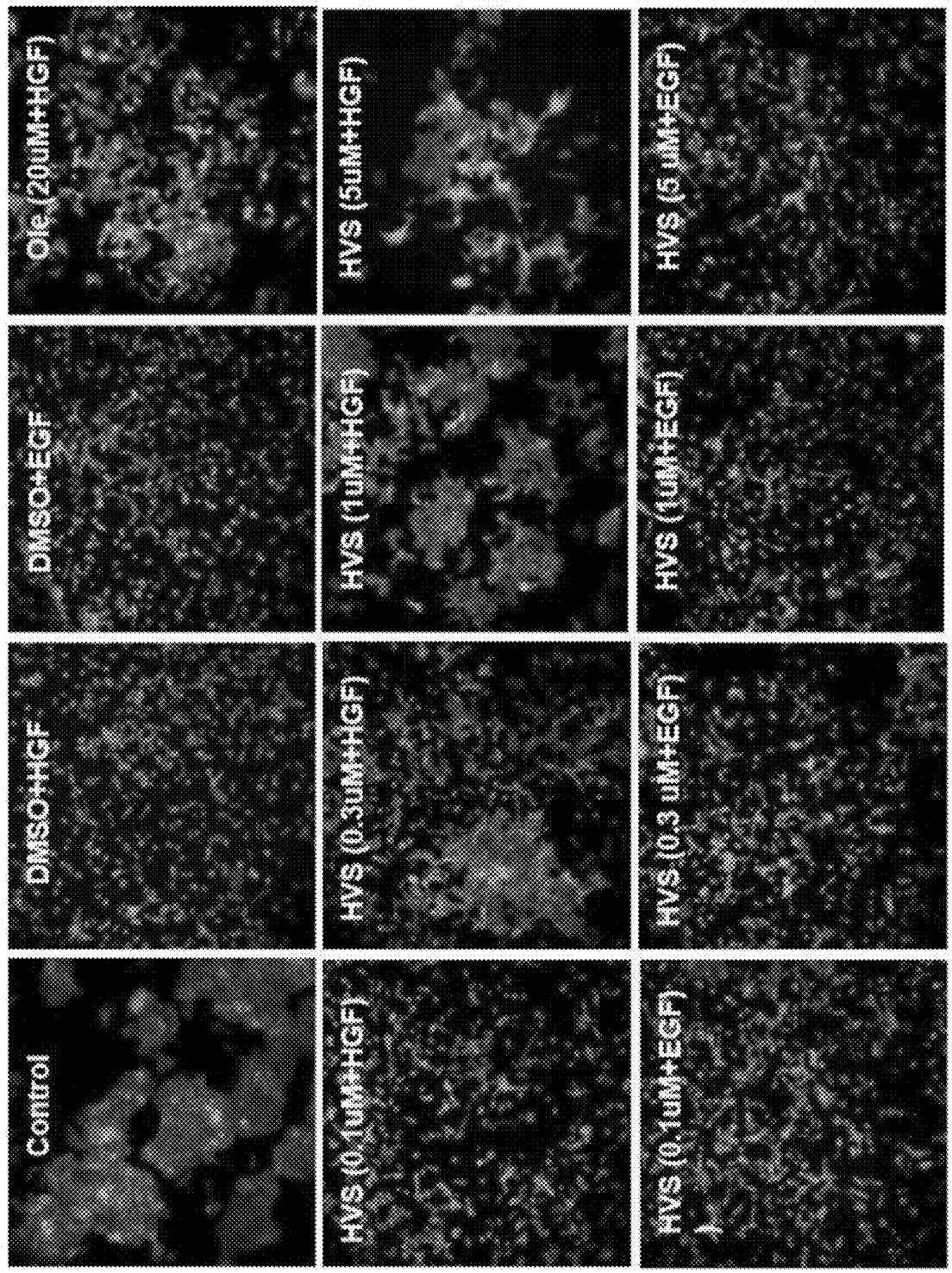
FIG. 6. (A) Effect of HVS on HGF-induced migration of the highly metastatic MDA-MB-231 human breast cancer cells in wound healing assay. Left panel shows quantitative analysis of the percentage of gap reduction (i.e., wound closure) in various treatment groups in MDA-MB-231 cancer cells. Vertical bars indicate the percentage of wound closure at 24 h after wounding, calculated relative to the wound distance at zero time±SEM of N=6 in each treatment group. SU11274 and (−)-oleocanthal were used as positive controls at 10 μM. Right panel represents photomicrographs of wound healing assay showing HVS treatment at three different concentrations (1.25, 2.5, and 5 μM) blocked the migration of MDA-MB-231 cells in response to HGF stimulation, as compared to DMSO as a vehicle control. (B) Effect of HVS on HGF-induced cell invasion of the highly aggressive MDA-MB-231 human breast cancer cells using Cultrex® BME cell invasion assay. The cells were treated with different concentrations of HVS for 24 h. Vertical bars indicate the percentage of cells invading the basement membrane at the end of treatment period±SEM of N=3 in each treatment group. (−)-Oleocanthal was used as a positive control at 20 μM dose.*P<0.05 as compared with vehicle-treated control. (C) Effect of HVS on HGF-induced scattering of the DU145 human prostate cancer cells in 2D monolayer cultures, compared to DMSO as vehicle control. Cells were treated with indicated concentrations of HVS for 30 minutes in serum-free media. 33 ng/mL HGF or 100 ng/mL EGF was spiked into the appropriate wells and cells were allowed to scatter for 16 h. Cells were fixed and stained with phalloidin. Representative 10× images are shown, N=3. (−)-Oleocanthal was used as a positive control at 20 μM dose.

In addition to its ability to inhibit c-Met-dependent cell proliferation, the inventors have also found that HVS appears to inhibit HGF-induced migration and invasion, which is likely a direct consequence of inhibition of c-Met activation (FIGS. 6A and 6B). Furthermore, HVS treatment significantly reduced the HGF-induced cell scattering of cancer cells in a dose-dependent manner, while similar treatment doses do not block cell scattering induced by EGF (FIG. 6C). Together, these data indicate that compounds 8-10 significantly impair the tumor cell motility and invasiveness mediated by the HGF/c-Met axis and, consequently, aggressive and metastatic phenotypes of cancer.

HVS was selected for further in vitro and in vivo studies. In a 2D similarity search of a database of small molecules with reported binding affinities against kinase targets, HVS does not have any significant sub-structural similarity to any known kinase inhibitors and thus, it represents a novel pharmacophore with this desirable biological property.

Figure 7B:
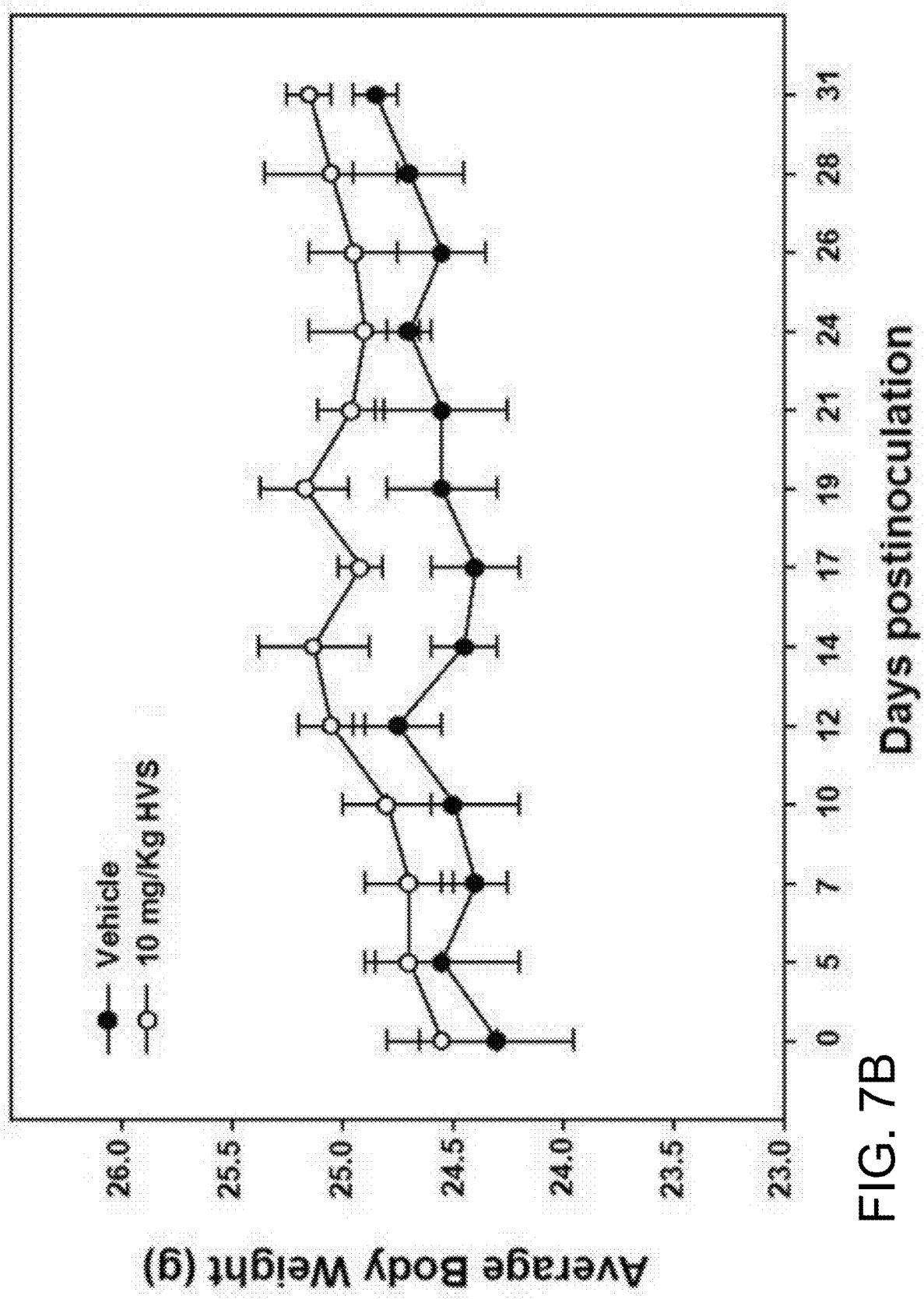
FIG. 7. The effect of HVS treatment on tumor growth in the human breast cancer xenograft model. Athymic nude mice with subcutaneous orthotopic MDA-MB-231/GFP human breast cancer cells were intraperitoneally injected with 10 mg/kg of HVS or the vehicle control. Treatment regimens were administered 3×/week, starting 5 days post-inoculation. (A) Left panel; tumor volume was evaluated periodically during treatment at the indicated days postinoculation. Tumor volume (V) was calculated by $V=(L\times W^2)/2$, where L was the length and W was the width of tumors. Points, the mean of tumor volume in mm$^3$ of several tumors (n=5) during the course of the treatment period; bars±SEM. *P<0.05 as compared to vehicle-treated control. Right panel; shown are two mice harboring human breast cancer. The mouse on the right shows the suppression of tumor growth with HVS treatment (10 mg/kg/day) compared to the vehicle-treated control mouse on the left. (B) No significant change in body weight was observed among treated animals, indicating the safety of HVS treatment. Error bars indicate SEM for n=5. (C) Left panel; vertical bars indicate mean tumor weight at the end of the experiment.*P<0.05 as compared to the vehicle-treated control. Error bars indicate SEM for n=5. Right panel; shows photomicrographs of primary breast tumors from mice with vehicle-treated cancer (left), and cancer treated with HVS at 10 mg/kg/day (right). (D) Protein expression of total and phosphorylated levels of c-Met in vehicle-treated or HVS-treated (10 mg/kg/day) breast tumors detected by Western Blot. (E-A and E-B) Left panel; immunostaining of sections obtained from vehicle-treated or HVS-treated (10 mg/kg/day) mice against Ki-67 (mitosis marker) and CD31 (endothelial marker) antibodies. Right panel; shows quantification of Ki-67 positive cells and microvessel density (MVD). Ki-67 positive cells in breast cancer tissues were examined in 5 areas at a magnification of ×200. MVD of breast tumor tissue sections was evaluated. Any CD31+ stained endothelial cell or endothelial cell cluster was counted as one microvessel. The mean microvessel count of the five most vascular areas was taken as the MVD, which was expressed as the absolute number of microvessels per 1.485 mm$^2$ (×200 field). Vertical bars indicate the average of 5 readings±SEM, *P<0.05 as compared with vehicle-treated controls.
Figure 7D:
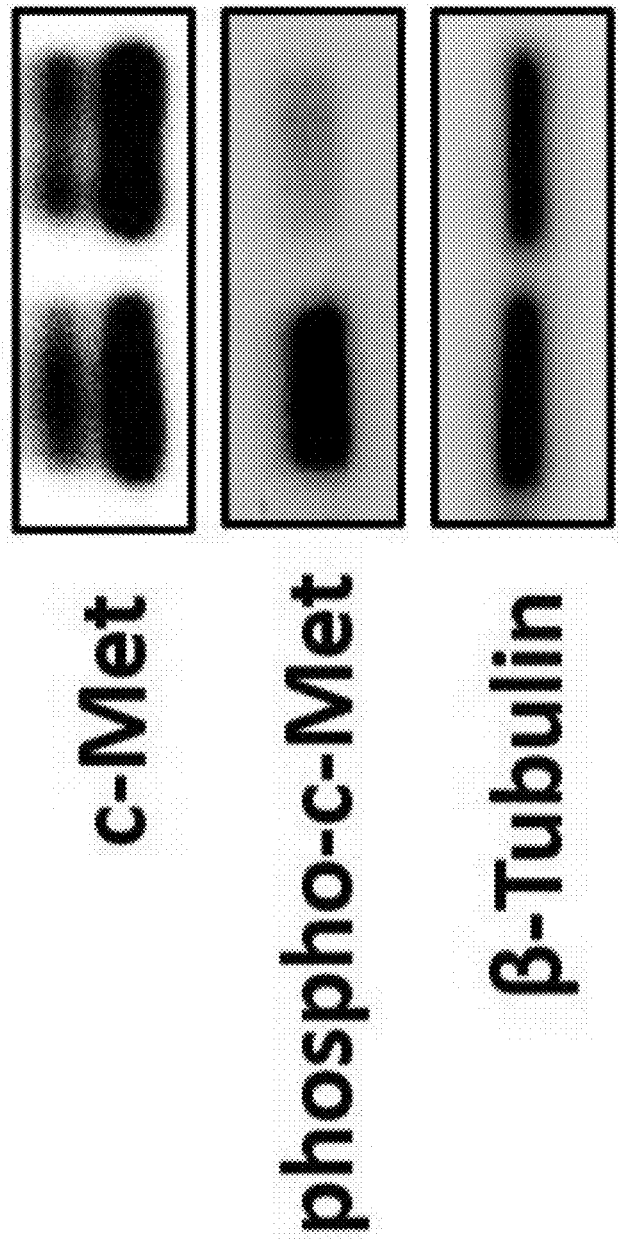

The safety profile of HVS has been assessed both in vitro and in vivo models. The results demonstrated that HVS is nontoxic to the non-tumorigenic human mammary epithelial cells up to concentrations 20-fold higher than its IC50 values in cell proliferation assay (FIG. 3D). A xenograft orthotopic athymic nude mouse model was generated using cells of the MDA-MB 231/GFP human breast cancer cell line (FIG. 6). Breast tumor growth was compared between animals dosed ip with 10 mg/kg of HVS (n=5), 3×/week, starting on the 5th day post-inoculation and continuing for 4 weeks, vs. non-treated animals in a control group (DMSO). Tumor progression was followed by direct measurement of tumor volume starting 14 days after orthotopic cell inoculation. HVS significantly reduced breast tumor volume and weight (FIG. 7), affecting a 92% reduction in tumor growth as compared to the vehicle-treated control group, without adversely affecting the treated mice's normal body weight gains. Western blot analysis of isolated tumor tissues showed relatively lower levels of p-c Met, compared to the control group, without change in total c Met levels (FIG. 7D). Immunohistochemical analysis of tumor specimens revealed that HVS suppressed both mitosis and new vessel formation, as evidenced by the suppression of the expression of their markers, Ki-67 and CD31, respectively (FIG. 7E).

In this animal model of breast cancer, 31 injected doses of HVS (10 mg/kg) did not cause any overt signs of toxicity without any observed significant body weight changes. These findings are of interest because they suggest the potential of HVS to selectively target malignant cells while lacking toxicity.

The durability of therapeutic responses to recent protein kinase inhibitors is limited by the emergence of drug resistance due to the occurrence of inhibitor-resistant mutant forms. Therefore, finding new inhibitors not only against the wild type but in addition against different mutant forms of a kinase are of significant therapeutic relevance. One mechanism by which c-Met deregulation leads to cancer is through gain-of-function mutations which are often correlated with poor clinical outcomes. Various MET activating point mutations have been implicated as the cause of hereditary papillary renal carcinoma (PRC) and were also detected in sporadic papillary renal carcinoma as well as in other carcinomas including lung cancers, head and neck cancers, childhood hepatocellular carcinoma, and gastric cancer. MET PRC mutant M1250T displayed the highest catalytic activity and thus, confers the highest neoplastic transforming potential. Clinical experience with small molecule kinase inhibitors has demonstrated that the selectivity of some of these inhibitors for wild-type versus mutant can be a cause of either primary drug resistance in case of pre-existing mutations or acquired resistance due to chronic treatment as represented by imatinib, which blocks wild-type Abl and c-Kit but inactive against several acquired mutations in chronic myelogenous leukemia and gastrointestinal stromal tumor patients. The c-Met small molecule inhibitor SU11274 can inhibit the activity of some c-Met mutants previously identified in hereditary papillary renal cell carcinoma patients, including H1094Y3 and M1250T, but other mutants such as L1195V and Y1230H were resistant.

The in vitro potencies of compounds 8-10 against the P+1 loop mutant M1250T is shown in FIG. 8. In the presence of 200 μM/L ATP, HVS is slightly more potent against this oncogenic human c-Met mutant, with $IC_{50}$ value of 0.9 μM, compared with the wild-type c-Met ($IC_{50}$ 1.0 μM) while compound 10 was almost equipotent with an $IC_{50}$ of ~0.4 μM in both wild and mutant types. The ability of compounds 8-10 to inhibit the oncogenic c-Met mutant M1250T broaden their therapeutic scope and possible use for aggressive tumor cell lines expressing c-Met constructs containing this activating mutation. A novel class of c-Met inhibitors represented by SU 11274 exhibited uncompromised inhibitory activity against this c-Met mutant but it has been limited to in vitro studies or brief in vivo studies without clinical significance due to its poor pharmaceutical properties and oral bioavailability. Lead chemicals, like compounds 8-10 are structurally distinct from SU 11274, with a new pharmacophore and have desirable biological properties as documented by our in vivo studies.

We have also examined the inhibitor nature of these novel compounds in prostate cancer cells. FIG. 6C indicates that the compound HVS appeared to block HGF-induced scattering of DU145 prostate cancer cells at low micromolar concentrations, while EGF induced scattering was not inhibited (results not shown).

FIG. 4B presents the results testing to determine which compound inhibited HGF-induced signaling in DU145 prostate cancer cells. DU145 prostate tumor cells were pretreated for 30 minutes with the indicated compounds. Following pretreatment, cells were pulsed for thirty minutes with HGF, cell lysates were prepared and western blot analysis was performed to identify pMet, pAkt, pErk and tubulin. As observed in FIG. 2, HVS was effective even at submicromolar concentrations. Compound 9 did not lower pMet induction but did attenuate pAkt signaling. Compound 10 actually appeared to increase Met dependent signaling while compound 11 had no effect.

Figure 9C:
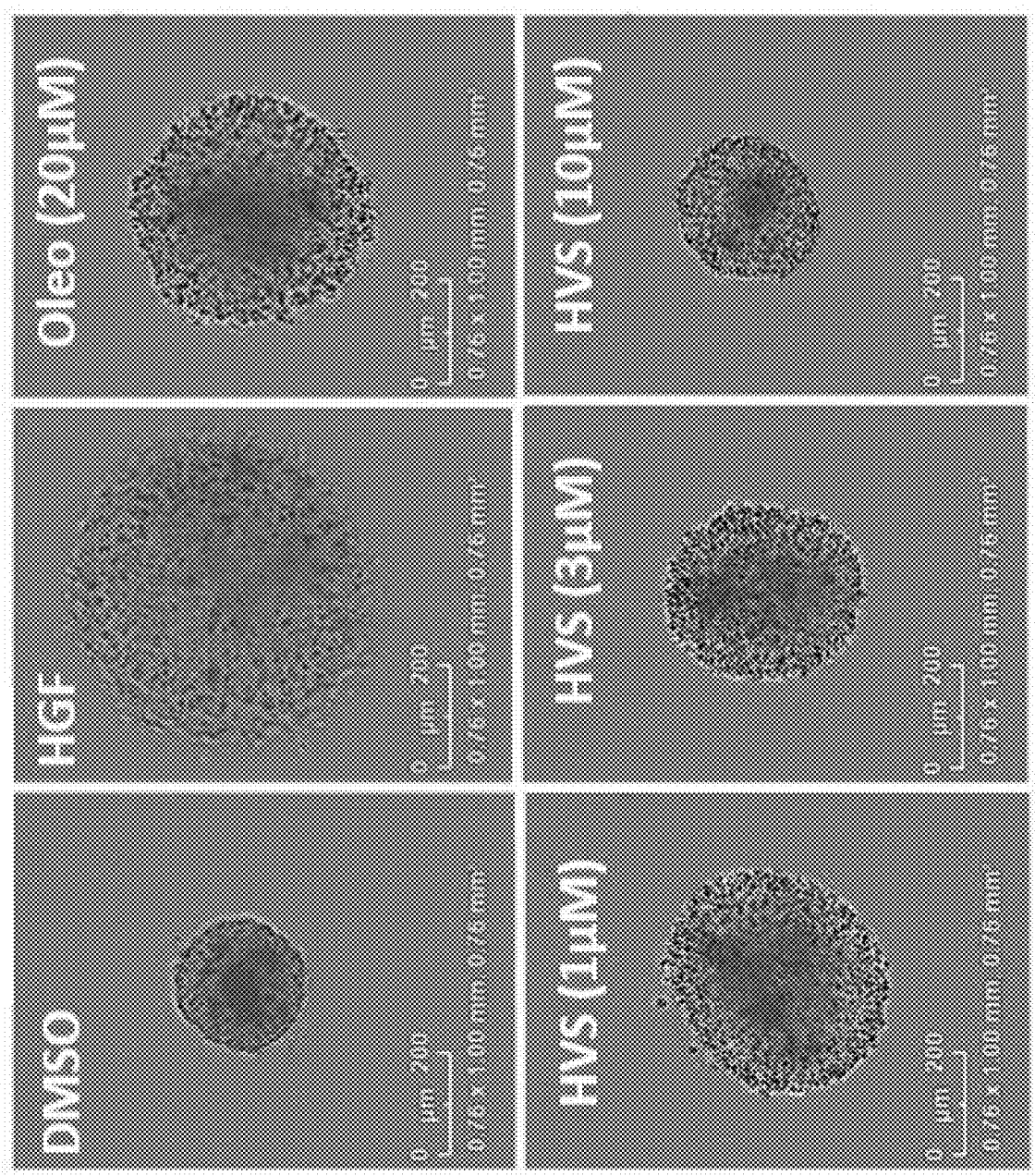
FIG. 9C: Visually representative spheroids that are quantitated in FIG. 9B.

To determine the effectiveness of these compounds under 3D growth conditions which more accurately predict effectiveness of new drugs in humans, DU145 spheroids were formed and allowed to grow for 72 hours. Images were recorded every 4 hours using the Incucyte platform. FIG. 9B indicates that compound 8 (HVS) blocked spheroid growth at concentrations as low as 1 micromolar in a dose dependent fashion with 10 micromolar reducing growth by over 80%. Compounds 9 and 10, at 10 micromolar reduced spheroid growth by about 50 percent (not shown).

Finally, 3D culturing approaches were used to determine if these compounds also blocked HGF induced growth of 231 spheroids. MDA-MB231 spheroids were all allowed to form and treated with compounds for up to 72 hours. Images were captured using the Incucyte platform. As observed for prostate tumor cells, compound 8 reduced growth in a dose dependent fashion, with 80% inhibition at 10 micromolar (FIG. 9A). Interestingly, compounds 9 and 10 at 10 micromolar were also effective (results not shown), suggesting these latter two derivatives may be more effective against Met pathways in breast cancer cells as compared to prostate cancer cells.

HVS was evaluated against a cross-section of tyrosine kinases (TKs), which are known to be structurally related and oncogenically relevant to c-Met, in order to understand its selectivity profile. A panel of 15 TKs was selected for biochemical analysis through the SelectScreen Kinase Profiling Service (Invitrogen, CA). In this assay, the results are expressed as % inhibition at a 10 µM dose (see Table I below). Significant inhibition (>50%) at 10 µM of HVS was observed for ABL1 and c-Met, with greatest relative inhibition for ABL1 (Table I). In contrast to its high potency against c-Met and ABL1, HVS barely inhibited other tested TKs activity, including the c-Met family member RON and the highly homologous, phylogenetically related kinase TYRO3 (3~4-fold selectivity difference versus c-Met, Table I). These results revealed that HVS demonstrated exquisite selectivity by selectively targeting two kinases, c-Met and ABL1, at pharmacologically relevant concentration, and suggested that HVS might be a promising c-Met/ABL1 dual kinase inhibitory hit.

| Kinase | Mean inhibition at 10 µM of HVS (%) |
| --- | --- |
| ABL1 | 79 |
| ALK | 21 |
| EGFR (ERbB1) | 7 |
| HER2 (ERbB2) | 4 |
| HER4 (ERbB4) | 7 |
| FGFR1 | 50 |
| FLT1 (VEGFR1) | 9 |
| IGF1R | −5 |
| KDR (VEGFR2) | 20 |
| KIT | −3 |
| MET (c-Met) | 72 |
| MST1R (RON0) | 15 |
| PDGFRβ | 14 |
| ROS1 | 24 |
| TYRO3 (RSE) | 21 |

Table I (Above) HVS was evaluated against a cross-section of tyrosine kinases (TKs), which are known to be structurally related and oncogenically relevant to c-Met, in order to understand its selectivity profile (Table 1). A panel of 15 TKs was selected for biochemical analysis through the SelectScreen Kinase Profiling Service (Invitrogen, CA). In this assay, the results are expressed as % inhibition at a 10 µM dose (Table 1). Significant inhibition (>50%) at 10 µM of HVS was observed selectively for ABL1 and c-Met, with greatest relative inhibition for ABL1 (Table 1). In contrast to its high potency against c-Met and ABL1, HVS barely inhibited other tested TKs activity, including the c-Met family member RON and the highly homologous, phylogenetically related kinase TYRO3 (3~4-fold selectivity difference versus c-Met, Table 1). These results revealed that HVS demonstrated exquisite selectivity by selectively targeting two kinases, c-Met and ABL1, at pharmacologically relevant concentration, and suggested that HVS might be a promising c-Met/ABL1 dual kinase inhibitory hit.

ABL1 is a member of the mammalian Abelson family of non-receptor TKs, which also includes ABL2. ABL1 was first identified as an oncogene required for the development of human leukemia initiated by retroviruses or chromosome translocations. ABL1 transduces diverse extracellular signals to protein networks that control proliferation, survival, migration, and invasion. Recent reports have uncovered roles for ABL kinases in solid tumors. Enhanced expression and activation of ABL1 kinase have been implicated in the progression of a wide variety of solid tumor types where c-Met activation also occurs, including breast and prostate cancers. In solid tumor cells, ABL1 activation has often been linked to upstream stimulation by hyperactive oncogenic RTKs and chemokine receptors. Activation of ABL1 kinase in NSCLC and breast cancer malignancies has been shown to occur downstream of the EGFR, HER2, and IGFR, as a late occurring event that contributes to the aggressive growth and metastasis of these solid tumors. Accordingly, ABL1 kinase can be considered as a point of convergence of the EGFR, HER2, and IGFR pathways and therefore it is an ideal target versus trying to inhibit three separate pathways. ABL1 was also proposed to interconnect oncogenic Met and p53 pathways in cancer cells. Based on these data, HVS would be capable of not only targeting its primary therapeutic target, c-Met, but also of interrupting multiple important pathways in solid tumor signaling, via blocking ABL1 activation, which adds a significant advantage over currently approved c-Met inhibitors in controlling aggressive phenotypes of solid tumors. Additionally, inhibition of ABL1 and c-Met sensitizes solid tumor cells to conventional agents and overcomes drug resistance developed to anticancer therapies already in clinical use, including EGFR and BRAF kinase inhibitors. Therefore, the inventors foresee that a dual c-Met/ABL1 inhibitor, such as HVS, could not only be initially effective in slowing tumor progression but also could prevent drug-resistant tumor growth and might be more effective if used in combination with chemotherapeutic agents for aggressive solid tumors phenotypes.

To identify the structural basis for HVS ABL1 affinity, additional docking simulation studies have been carried out using Glide XP (Schrödinger 2014). Interactions of HVS with TKs for which it demonstrated the highest and lowest affinities, including ABL1 (69% inhibition), c-Met (62% inhibition) and IGF1R (no observed inhibition) were studied. Both docking scoring functions available in Glide, ChemScore and GlideScore, were used since the combination of multiple scoring functions provide better prediction and correlation between docking scores and ligand affinity. The binding site of each kinase was evaluated by calculating various properties using the program SiteMap (SiteMap 2.9, Schrödinger 2014) to better understand functional groups contributed to binding differences.

HVS fits very well in the binding site of ABL1 kinase, displaying proper complementarity to the receptor and forming several critical interactions predicted to stabilize the kinase domain in its inactive conformation and thus, prevents its ATP activation. Docking of HVS into ABL1 kinase revealed a HB interaction between its C-6' phenolic hydroxyl and the backbone carbonyl of Thr319 in the hinge region. Additionally, the ester carbonyl contributed a critical HB interaction with the backbone of Met318 at the hinge region while the aromatic C-7 phenolic hydroxyl group formed a HB with the side chain carboxylate of Glu286. Furthermore, the terminal aromatic ring A of HVS is oriented along the surface edge of the binding site, making a strong p-p stacking interaction with Tyr253, which has an important role in stabilizing the inactive form of the kinase. HVS binds to ABL1 domain via four important interactions whereas it exhibited three interactions upon binding to wild-type c-Met and its oncogenic variant, which might explain, at least in part, the improved activity and selectivity to ABL1 compared to c-Met.

The hydrophobic pocket where HVS fits is deeper and larger in ABL1 than in c-Met, as illustrated by comparing the properties of both sites which showed that the volume and size of ABL1 binding site are significantly larger compared to c-Met. The larger and deeper pocket of ABL1 allowed an exceptional fitting of the HVS, facilitating several favorable interactions with Val256, Ala269, Leu370, Ala380, Phe317, Val299, and Phe382 which in turn, stabilized the bioactive U-shaped conformation and confer a substantial binding affinity towards ABL1. These observations can explain the higher docking score and improved activity of HVS against ABL1 compared to c-Met. However, the c-Met pocket was still able to accommodate HVS with a small conformational shift due to the plasticity of this kinase in molding the activation and nucleotide-binding loops to the shape of the ligand in the binding site. In contrast, the aforementioned hydrophobic pocket was very shallow or essentially nonexistent in IGF1R as confirmed by the calculated volume of the site, and thus, HVS has been imperfectly docked upside down with its main scaffold outside the binding site, unable to demonstrate critical interactions with the protein, consistent with the low observed activity and docking score for this kinase.

A therapeutically effective dosage for administering HVSAs to mammals to treat cancer ranges from 0.1 to 100 mg/kg, 1.0 to 50 mg/kg, and preferably 10 to 20 mg/kg. HVS was administered i.p to a nude mouse model at a dose of 10 mg/kg 3×/week showing 92% tumor growth inhibition, compared to the vehicle-treated group at the end of the study. This dose is expected to be reduced at least to 5 mg/Kg or 2.5 mg/Kg, especially if combined with other cancer fighting drugs and/or used daily.

Combination therapy. Multiple combination directions a likely to be effective with the HVSAs. HVSAs may be combined with other HVSAs. As dual Met/ABL1 inhibitors HVSAs will likely synergize the cytotoxicity of taxanes including paclitaxel/docetaxel and the dual EGFR-HER2 inhibitor lapatinib. HVSAa can be combined with chemotherapeutic agents such as doxorubicin and paclitaxel. HVSAs can be also combined with other approved c-Met inhibitors such as crizotinib and cabozantinib to reduce their effective doses and overcome their acquired resistance. HVSAs can be also combined with marketed EGFR inhibitors such as gefitinib and erlotinib to overcome the acquired resistance due to EGFR/Met cross-talk commonly observed in NSCLC patients after prolonged treatment periods. Due to its ABL kinase inhibitory activity, HVSAs can be also combined with ABL inhibitors such as imatinib or nilotinib. A preferable goal of these combinations is not only to slow tumor progression but also to prevent drug-resistant tumor growth.

Alternative forms of HVSAs are represented by Chem./compounds 20 and 21.

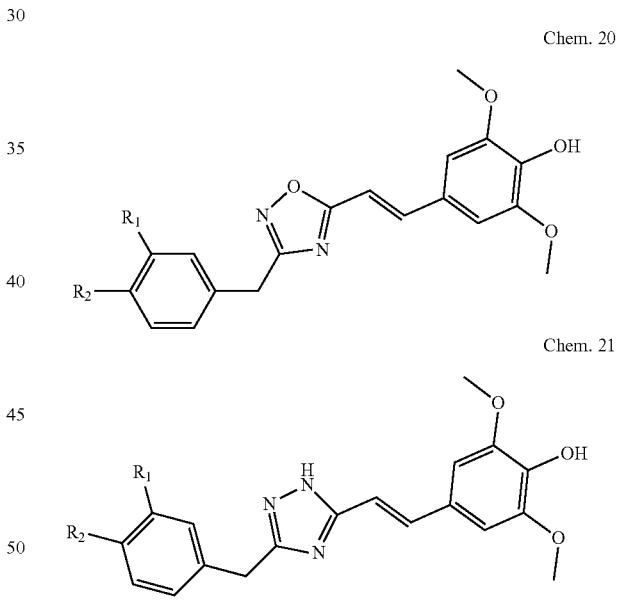

The inventors have encouraging in silico data regarding these two chemicals (20 and 21) to be the new generation of HVSAs. These chemical groups wold follow similar substitution of as the ester HVSAs above. Based on extensive docking studies, the ester moiety in HVS appeared not to contribute any binding role, yet it provided the proper molecular size and spatial conformation alignment necessary for adequate fitting at the binding pocket. Meanwhile, the ester functionality is not favorable due to its metabolic instability and liability to carboxylesterases cleavage. Therefore, it has been proposed that replacing the ester linker in HVS with different bioisosteric heterocycles such as oxadiazole in compound 20 and triazole in compound 21 could mimic the spatial conformation adopted by an ester linker, whilst lacking metabolic stability concerns associated with the ester functionality, and maintain or improve the activity of HVS against c-Met kinase. However, a previous oxadiazole analog compound 12 has been synthesized during the SAR studies of HVS, in an attempt to find a suitable ester isostere, and it was not active in biochemical assays against c-Met kinase. Interestingly, docking studies were able to clearly explain why compound 12 was not active against c-Met kinase (FIG. 10A). compound 12 was just able to get inside the pocket via its tyrosol moiety, which formed a HB through its phenolic hydroxyl group with the phenolic hydroxyl of the Tyr1230 side chain, leaving the sinapate moiety outside the pocket (FIG. 10A). Such binding pose hindered compound 12 from interacting with critical residues in the hinge region and thus, compound 12 totally lost its c-Met inhibitory activity. This was mainly attributed to the lack of the required flexibility in the linker to adopt a shallow U-shaped conformation within the kinase pocket, which is important for maintaining the c-Met inhibitory activity. To prove this hypothesis, a methylene group has been added to connect between aromatic ring A of compound 12 and its oxadiazole group, in order to afford the desired flexibility in the linker (Chem. 20, above). The binding pose of the newly proposed analog compound 20 is shown in FIG. 10B. Additionally, an overlay study has been conducted to compare compound 20's binding pose to that of the inactive one (compound 12) in order to validate the design hypothesis (FIG. 10A). As shown earlier, compound 12 barely entered the binding site and missed the critical interactions with the hinge (FIG. 10A). In contrast, compound 20 showed perfect fitting within the c-Met kinase pocket and satisfied all the required interactions with both the hinge as well as the activation loop (FIG. 10). Importantly, compound 20 maintained the same predicted binding pose of HVS; firstly, compound 20 engaged in a critical HB with the hinge via its amino group, mimicking the C-6' hydroxyl group of HVS, secondly, compound 20 maintained the HB interactions exerted by the sinapate moiety within the c-Met's activation loop, and finally, compound 20 showed perfect fitting within the c-Met's hydrophobic subpocket via its C-7' isopropyl group (R1), mimicking the binding role of the C-5' methoxy group of HVS but with much better filling of the hydrophobic space (FIG. 10). It was interesting to note that compound 20's oxadiazole ring was involved in a strong π-π stacking with Tyr1230, adding a further advantage for the oxadiazole functionality of compound 20 over the ester group of HVS which did not demonstrate any direct binding role within the c-Met kinase pocket (FIG. 10B). Compound 21 showed a nearly identical binding pose to that of compound 20 within the c-Met kinase binding site.

Preparation of HVSAs. The HVSAs are prepared as follows. The ester HVSAs such as compounds 8-10, and 14-19, are prepared by convenient one-step chemical synthesis using the highly chemoselective Mitsunobu esterification reaction (Scheme 1, below).

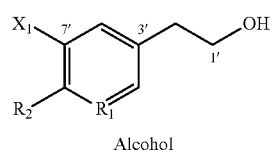

Alcohol

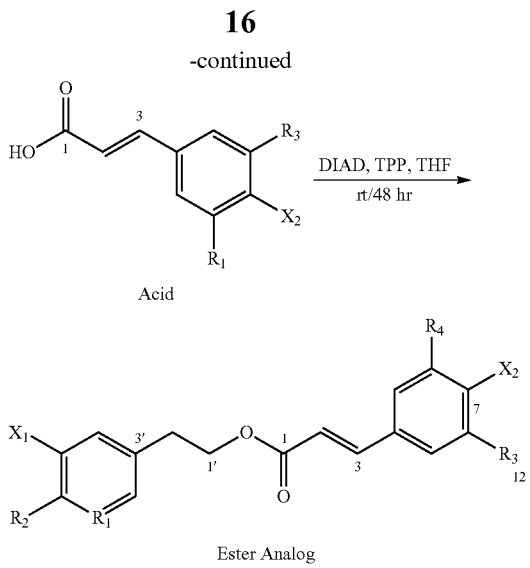

Acid

Ester Analog

In a similar fashion, the proposed bioisotere 1,2,4-oxadiazole HVSAs can be synthesized via condensation reactions involving sinapic acid and the substituted-acetimidamide oxime (Scheme 2, below)

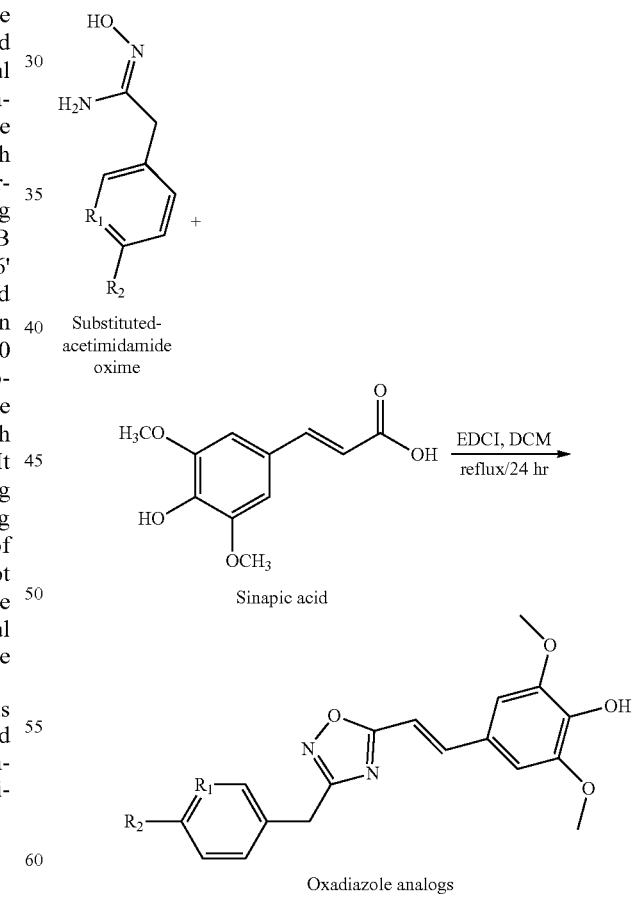

Substituted-acetimidamide oxime

Sinapic acid

Oxadiazole analogs

In a similar fashion, the proposed bioisotere triazole HVSAs can be synthesized via condensation reactions involving sinapic acid and the substituted acetohydrazonamide (Scheme 3, below).

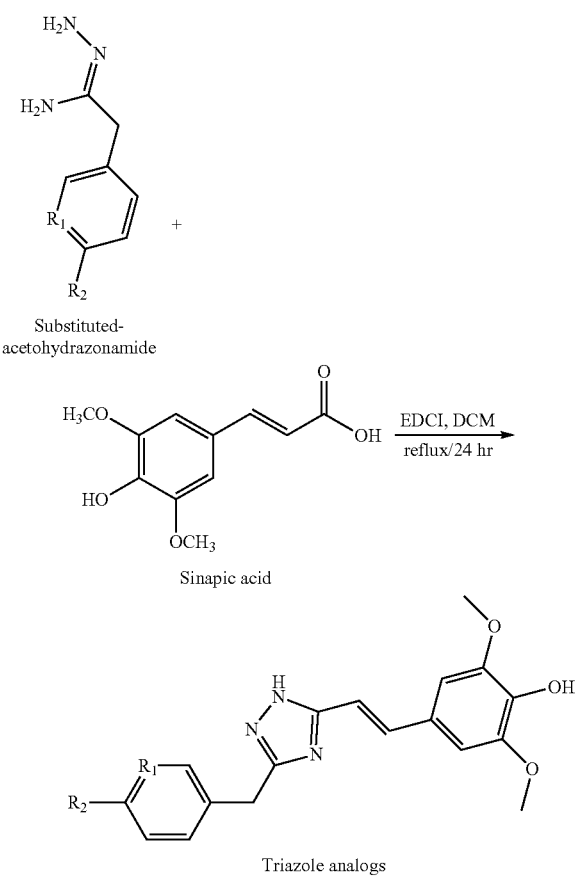

Cancers and Precancers: HVSAs showed effectiveness against both cMet and Abl1 dependent/influenced cancers/precancers. As evidenced by such effectiveness, and based on the mechanisms of the therapeutic action of the HVSAs, these compounds should additionally be effective against various human and mammalian cancers listed above, and additionally colon, gastric, bladder, breast, prostate, ovarian, pancreatic, kidney, renal, liver, lung, including small cell lung carcinomas and non-small cell lung carcinomas, head and neck, thyroid, and prostate cancers as well as sarcomas, hematologic malignancies, melanoma, and central nervous system tumors. Due to its ability to inhibit c-Met mutant variants, HVSAs can be also effective against, for example, hereditary papillary renal cell carcinoma which overexpress the mutant proteins.

The term "precancer" includes a precancerous condition, also called a premalignant condition or a potentially precancerous condition or potentially premalignant condition, is a state of disordered morphology of cells that is associated with an increased risk of cancer. Typically, if left untreated, this condition may lead to cancer. Such condition is usually either dysplasia or benign neoplasia. The term "precancer" may also include carcinoma in situ, which is a noninvasive cancer that has not progressed to an aggressive, invasive stage, noting that not all carcinoma in situ will progress to invasive disease. The term "precancer" also includes premalignant lesions, including morphologically atypical tissue which appears abnormal under microscopic examination, and in which cancer is more likely to occur than in its apparently normal counterpart. Nonlimiting examples of premalignant conditions include actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia.

Crizotinib (PF-02341066), Cabozantinib (XL184, BMS-907351), Foretinib (GSK1363089), PHA-665752, SU11274, SGX-523, BMS-777607, Tivantinib (ARQ 197), JNJ-38877605, PF-04217903, MGCD-265, Capmatinib (INCB28060), BMS-754807, BMS-794833, AMG-208, MK-2461, Golvatinib (E7050), AMG-458, Tepotinib (EMD 1214063), NVP-BVU972, and NPS-1034, and a pharmacologically acceptable salt, solvate, ester, amide, clathrate, stereoisomer, enantiomer, prodrug or analog thereof, or a combination thereof.

In further embodiments a first further pharmaceutically active agent is one or more of (1) additional HVSA distinct from the first pharmaceutically active agent, (2) a receptor tyrosine kinase inhibitor (RTKi), (3) an agent that targets non-receptor tyrosine kinases, (4) an anti-cell proliferative chemotherapeutic agent, or of a pharmacologically acceptable salt, solvate, ester, amide, clathrate, stereoisomer, enantiomer, prodrug or analog thereof. Further embodiments comprise the step of administering to the patient a therapeutically effective amount of a second further pharmaceutically active agent, where the second pharmaceutically active agent is a further one of an HVSA and a pharmacologically acceptable salt, solvate, ester, amide, clathrate, stereoisomer, enantiomer, prodrug or analog thereof, or a combination thereof, and the first pharmaceutically active agent is distinct from the second pharmaceutically active agent. In further embodiments the first pharmaceutically active agent is a HVSA that has been chemically modified to increase one of bioavailability. In further embodiments the pharmaceutically active agent is in a cyclodextrin conjugation. In further embodiments the cyclodextrin conjugation is one of an α-cyclodextrin (α-CD) conjugation, a β-cyclodextrin (β-CD) conjugation, and a γ-cyclodextrin (γ-CD) conjugation. In further embodiments the pharmaceutically active agent is formed as nanoparticles. In further embodiments the nanoparticles are formed using solution-enhanced dispersion by supercritical carbon dioxide.

The invention further relates to methods and therapeutic products including a first pharmaceutically active agent being one of an HVSA, and a pharmacologically acceptable salt, solvate, ester, amide, clathrate, stereoisomer, enantiomer, prodrug or analog thereof, or a combination thereof; and a further pharmaceutically active agent.

In further embodiments the further pharmaceutically active agent is one or more additional HVSAs, or a pharmacologically acceptable salt, solvate, ester, amide, clathrate, stereoisomer, enantiomer, prodrug or analog thereof, distinct from the first pharmaceutically active agent. In further embodiments the further pharmaceutically active agent is one or more receptor tyrosine kinase inhibitors; a receptor tyrosine kinase inhibited is one of c-Met, RON, ROS, EGFR1, EGFR2, EGFR3, EGFR4, EGRFvIII, c-Kit, c-FMS, FLT3, PDGFR, IGFR, VEGFR, VEGR2, TIE-1, TIE-2, PTK-7, FGFR1-3, TRKA-C, RORs, BCR-ABL, EPHA1-5, EPHB1-4, and RET; and the receptor tyrosine kinase inhibitor is one of Alectinib, Axitinib, Crizotinib, Cabozantinib, Centinib, Erlotinib, Gefitinib, Lapatinib, Lenvatinib, Osimertinib, Pazopanib, Ponatinib, Regorafenib, Sorafenib, Sunitinib, Tofacitinib, Vandetanib, and Vismodegib. In further embodiments the further pharmaceutically active agent is one or more agents that target non-receptor tyrosine kinases; the non-receptor tyrosine kinase is one of ABL1-2, ACK1, BLK, Bmx, bRAF, BRK, BTK, CSK, FAK, FES, FRK, FYNA, HCK, ITK, Jak1-2, LCK, Lok1, LRRK2, LYNA-B, MNK1, MEK, mTOR, PI3K, PYK2, Src, Syk, Zap-70, and CDK4; and the agent that targets the non-receptor tyrosine kinase is one of Bosultinib, Cobimetinib, Dabrafenib, Dasatinib, Everolimus, Ibrutinib, Idelalisib, Imatinib, nilotinib, Palbociclib, Ponatinib, Rogorafenib, Ruxolitinib, Temsirolimus, and Trametinib. In further embodiments the further pharmaceutically active agent is one or more anti-cell proliferative chemotherapeutic agent and the anti-cell proliferative chemotherapeutic agent is one of an anti-cancer and anti-tumor drug; an alkylating agent, anti-metabolite, plant extract, plant alkaloid, nitrosourea, hormone, nucleoside analog, and nucleotide analog; and 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), Nab-paclitaxel, vinblastine, vincristine, doxorubicin, dibromomannitol, irinotecan, topotecan, etoposide, teniposide, or pemetrexed.

As used herein, the term "active agent" includes the one of the HVSAs as described herein. The term active agent may also be referred to as the active compound, active ingredient, active material, the inventive compound and/or the active drug substance.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active results from the use of an enteric coating of an oral medication (e.g., an oral dosage form).

The term an "effective amount" of an agent, as used herein, includes that amount sufficient to effect beneficial or desired results, such as clinical results, and, as such, an "effective amount" depends upon the context in which it is being applied.

The terms "extended release" or "sustained release" interchangeably includes a drug formulation that provides for gradual release of a drug over an extended period of time, e.g., 6-12 hours or more, compared to an immediate release formulation of the same drug. Preferably, although not necessarily, extended release results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof.

Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release," as used herein, includes that the agent (e.g., an HVSA, or any pharmacologically acceptable salt, solvate, ester, amide, clathrate, stereoisomer, enantiomer, prodrug, or analog thereof, or a combination thereof), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing an active agent described herein (e.g., an HVSA, or any pharmacologically acceptable salt, solvate, ester, amide, clathrate, stereoisomer, enantiomer, prodrug, or analog thereof, or a combination thereof), formulated with a pharmaceutically acceptable excipient, and typically manufactured or sold with the approval of a governmental regulatory agency as part of a therapeutic regimen for the treatment of disease in a mammal, especially with the mammal being a human. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes an ingredient other than the active agents described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., cancer), or may refer to a treatment of a pre-disease state. Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of an HVSA, or any pharmacologically acceptable salt, solvate, ester, amide, clathrate, stereoisomer, enantiomer, prodrug, or analog thereof, or a combination thereof.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Pharmaceutical Compositions:

The methods described herein can also include the administrations of pharmaceutically acceptable compositions that include the HVSAs, or any pharmacologically acceptable salt, solvate, ester, amide, clathrate, stereoisomer, enantiomer, prodrug, or analog thereof, or a combination thereof. Pharmaceutical compositions and dosage forms of the invention comprise one or more active ingredients in relative amounts and formulated so that a given pharmaceutical composition or dosage form inhibits cancer cell proliferation or other disease or condition where inhibiting the hepatocyte growth factor receptor can therapeutically influence the respective disease or condition progression. Preferred pharmaceutical compositions and dosage forms comprise an HVSA, or any pharmacologically acceptable salt, solvate, ester, amide, clathrate, stereoisomer, enantiomer, prodrug, or analog thereof, or a combination thereof, optionally in combination with one or more additional active agents. When employed as pharmaceuticals, any of the present active agents can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention (e.g. the HVSAs, or any pharmacologically acceptable salt, solvate, ester, amide, clathrate, stereoisomer, enantiomer, prodrug, or analog thereof, or a combination thereof) can be administered alone, combined, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

The pharmaceutical compositions can be formulated so as to provide immediate, extended, or delayed release of the active ingredient after administration to the patient by employing procedures known in the art.

In addition to the dosages above, the pharmaceutical compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the active agent may be mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration.

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active agent by controlling the dissolution and/or the diffusion of the active agent substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the administered therapeutic or drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings:

The pharmaceutical compositions formulated for oral delivery, such as tablets or capsules of the present invention can be coated or otherwise compounded to provide a dosage form affording the advantage of delayed or extended release. The coating may be adapted to release the active agent in a predetermined pattern (e.g., in order to achieve a controlled release formulation) or it may be adapted not to release the active agent until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the active agent is released in the lower gastrointestinal tract.

In addition to coatings that effect delayed or extended release, the solid tablet compositions may include a coating adapted to protect the composition from unwanted chemical changes (e.g., chemical degradation prior to the release of the active agent). The coating may be applied on the solid dosage form in a similar manner as that described in *Encyclopedia of Pharmaceutical Technology*, vols. 5 and 6, Eds. Swarbrick and Boyland, 2000.

Parenteral Administration:

Within the scope of the present invention are also parenteral depot systems from biodegradable polymers. These systems are injected or implanted into the muscle or subcutaneous tissue and release the incorporated active agent over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery:

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences,* 81(1): 1-10, 1992)

Oral transmucosal absorption is generally rapid because of the rich vascular supply to the mucosa and allows for a rapid rise in blood concentrations of the therapeutic or active agent ("American Academy of Pediatrics: Alternative Routes of Drug Administration—Advantages and Disadvantages (Subject Review)," *Pediatrics,* 100(1):143-152, 1997).

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art.

Formulations for sublingual administration can also be used, including powders and aerosol formulations. Exemplary formulations include rapidly disintegrating tablets and liquid-filled soft gelatin capsules.

Dosing Regimens:

The present methods for treating cancer are carried out by administering one or more HVSAs, or any pharmacologically acceptable salt, solvate, ester, amide, clathrate, stereoisomer, enantiomer, prodrug, or analog thereof, or a combination thereof for a time and in an amount sufficient to result in stabilization and/or reversal of cancer symptoms, or other disease or condition where inhibiting the hepatocyte growth factor receptor can therapeutically influence the respective disease or condition progression. The amount and frequency of administration of the compositions can vary depending on, for example, what is being administered, the state of the patient, and the manner of administration. The dosage is likely to depend on such variables as the type and extent of progression of the cancer, the severity of the cancer, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of cancer or slowing its progression.

The amount of active agent per dose can vary. For example, a subject can receive from about 0.1 µg/kg to about 50,000 µg/kg. Generally, the active agent is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of an active agent (e.g., 0.089-3.9 mmol) or 0.1-50 µmol of an active agent (e.g., 0.1-25 µmol or 0.4-20 µmol).

The frequency of treatment may also vary. The subject can be treated one or more times per day with the active agent (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

KITS: Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce incidence, duration, and or severity of cancer, cell proliferation disorder, or other disease or condition where inhibiting the hepatocyte growth factor receptor can influence the respective disease or condition progression.

We claim:

1. A method of treating cancer in a mammal in need thereof comprising
   administering a therapeutically effective amount of a therapeutic;
   wherein the therapeutic is (E)-4-hydroxy-3-methoxyphethyl 3-(4- hydroxy-3, 5-dimethoxyphenyl) acrylate, a pharmacologically acceptable salt thereof, or a combination thereof;
   wherein the cancer is a breast cancer.

2. The method of claim 1, wherein the therapeutic inhibits c-Met kinase.

3. The method of claim 1 wherein the therapeutic is administered at a dose of between 2.5 mg/kg and 10 mg/kg, to mammal mass.

4. The method of claim 1 wherein the therapeutic is administered at a dose of at 1.0 to 10 mg/kg to mammal mass.

5. The method of claim 1 wherein the therapeutic is administered at a dose of between 0.10 mg/kg and 100 mg/kg, to mammal mass.

6. The method of claim 1 wherein the therapeutic is administered at a dose of between 1.0 mg/kg and 50 mg/kg, to mammal mass.

7. The method of claim 1 wherein the therapeutic is administered at a dose of between 10 mg/kg and 20 mg/kg, to mammal mass.

8. The method of claim 1 wherein the mammal is a human.

9. A method of treating cancer in a mammal in need thereof the therapeutic inhibits c-Met kinase comprising:
   administering a therapeutically effective amount of a therapeutic;
   wherein the therapeutic is (E)-4-hydroxy-3-methoxyphethyl 3-(4- hydroxy-3, 5-dimethoxyphenyl) acrylate, a pharmacologically acceptable salt thereof, or a combination thereof;
   the cancer is a c-Met influenced breast cancer;
   the mammal is human; and
   the therapeutic is administered at a dose of between 0.10 mg/kg and 100 mg/kg.

* * * * *